(12) United States Patent
Smith et al.

(10) Patent No.: US 11,376,367 B2
(45) Date of Patent: Jul. 5, 2022

(54) ASSEMBLY FOR A MEDICATION DELIVERY DEVICE AND MEDICATION DELIVERY DEVICE

(71) Applicant: NORTON HEALTHCARE LIMITED, Castleford (GB)

(72) Inventors: Christopher James Smith, Prenton (GB); Dale Marc Comley, Parchwich (GB); Lee Thomas Smith, Tixall (GB)

(73) Assignee: NORTON HEALTHCARE LIMITED, Castleford (GB)

( * ) Notice: Subject to any disclaimer, the term of this patent is extended or adjusted under 35 U.S.C. 154(b) by 125 days.

(21) Appl. No.: 16/483,142

(22) PCT Filed: Jan. 25, 2018

(86) PCT No.: PCT/EP2018/051876
§ 371 (c)(1),
(2) Date: Aug. 2, 2019

(87) PCT Pub. No.: WO2018/141634
PCT Pub. Date: Aug. 9, 2018

(65) Prior Publication Data
US 2019/0374721 A1    Dec. 12, 2019

(30) Foreign Application Priority Data

Feb. 3, 2017 (EP) .................................... 17154622

(51) Int. Cl.
*A61M 5/31* (2006.01)
*A61M 5/315* (2006.01)
*A61J 1/14* (2006.01)

(52) U.S. Cl.
CPC ........ *A61M 5/3146* (2013.01); *A61M 5/3156* (2013.01); *A61M 5/3157* (2013.01);
(Continued)

(58) Field of Classification Search
CPC ............ A61M 5/3146; A61M 5/31535; A61M 5/31553; A61M 5/3156; A61M 5/3157;
(Continued)

(56) References Cited

U.S. PATENT DOCUMENTS 5,226,895 A    7/1993 Harris
2006/0270985 A1    11/2006 Hommann et al.
(Continued)

FOREIGN PATENT DOCUMENTS

CH    WO 2016033701 A1 *  3/2016  .......... A61M 5/3158
DE       102004045326 A1    11/2005
(Continued)

*Primary Examiner* — James D Ponton
(74) *Attorney, Agent, or Firm* — David S. Safran; Roberts Calderon Safran & Cole, P.C.

(57) ABSTRACT

An assembly for a medication delivery device, wherein the assembly is configured to perform a dose setting operation, the assembly having a dose setting sleeve and a drive sleeve, wherein the dose setting sleeve has a first dosing track having a first length and defining a first size of a dose and a second dosing track having a second length and defining a second size of a dose, wherein the first length is different from the second length and the first size is different from the second size. The drive sleeve has an engagement feature configured to engage with one of the dosing tracks. The assembly is configured such the dose setting operation has a first step wherein the engagement feature is aligned with one of the dosing tracks and a second step wherein the engagement feature is moved along the dosing track.

15 Claims, 8 Drawing Sheets

(52) U.S. Cl.
CPC .... *A61M 5/31535* (2013.01); *A61M 5/31553* (2013.01); *A61J 1/1406* (2013.01); *A61M 5/3158* (2013.01); *A61M 2205/581* (2013.01); *A61M 2205/584* (2013.01)

(58) Field of Classification Search
CPC .......... A61M 5/3158; A61M 2205/581; A61M 2205/584; A61J 1/1406
See application file for complete search history.

(56) References Cited

U.S. PATENT DOCUMENTS

| | | |
|---|---|---|
| 2007/0167921 A1* | 7/2007 | Burren et al. ...... A61M 5/3158 604/211 |
| 2009/0054846 A1 | 2/2009 | Moser et al. |
| 2010/0010454 A1 | 1/2010 | Marshall et al. |
| 2012/0203184 A1 | 8/2012 | Selz et al. |
| 2012/0316508 A1 | 12/2012 | Kirchhofer |
| 2015/0250950 A1 | 9/2015 | Moser et al. |
| 2016/0175528 A1 | 6/2016 | Marshall et al. |
| 2016/0367760 A1 | 12/2016 | Bainton et al. |

FOREIGN PATENT DOCUMENTS

| | | |
|---|---|---|
| EP | 0496141 A1 | 7/1992 |
| WO | 9004423 A1 | 5/1990 |
| WO | 2011088894 A1 | 7/2011 |
| WO | 2012118687 A1 | 9/2012 |
| WO | 2016033701 A1 | 3/2016 |

\* cited by examiner

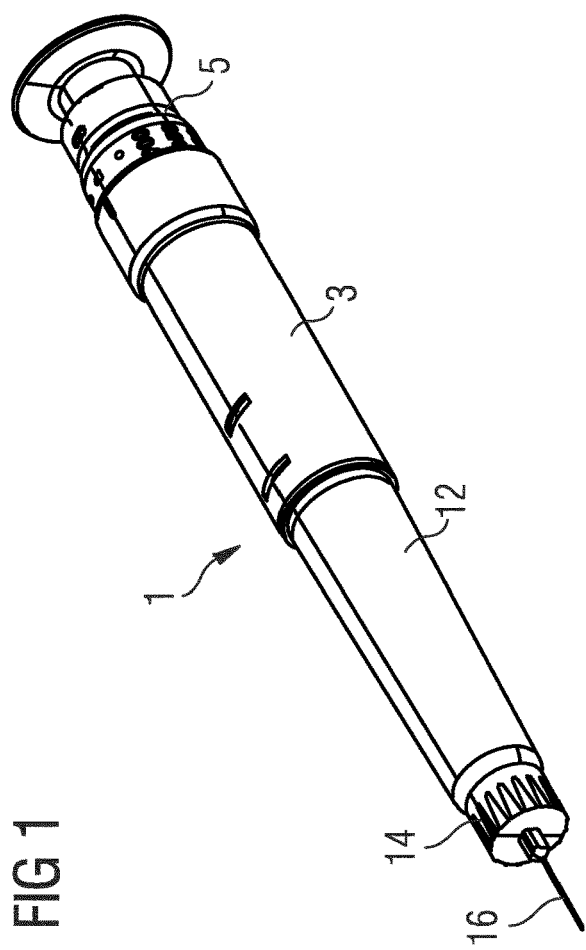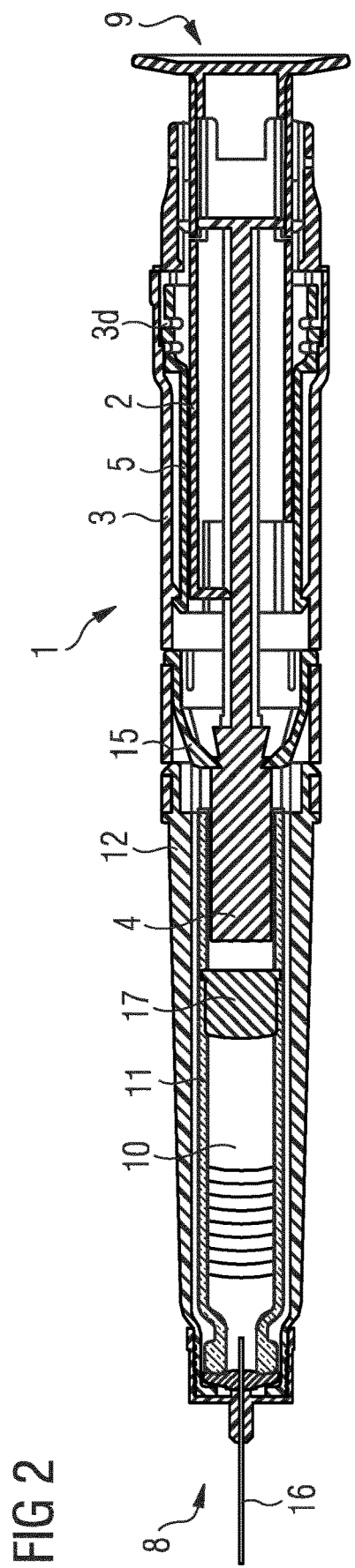

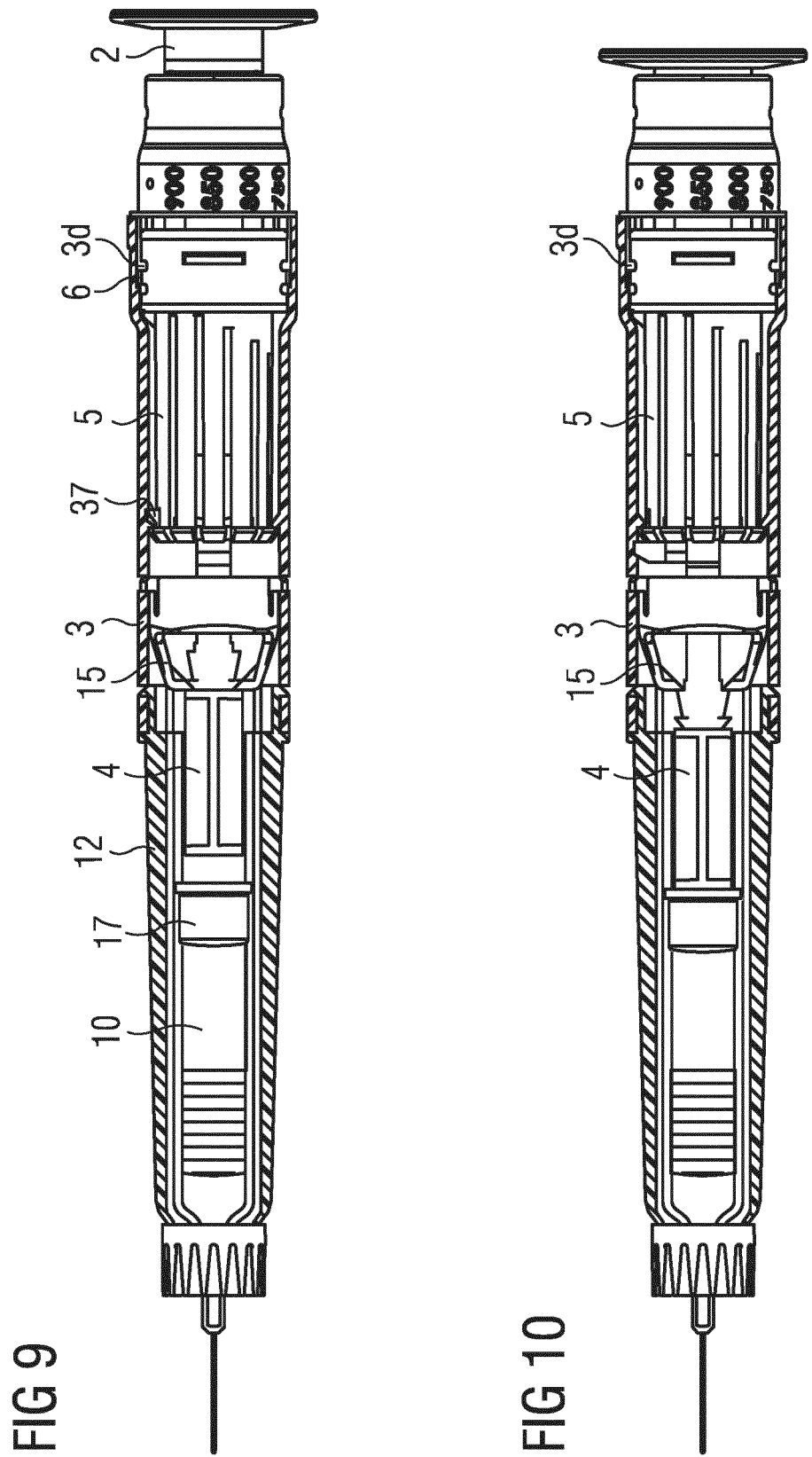

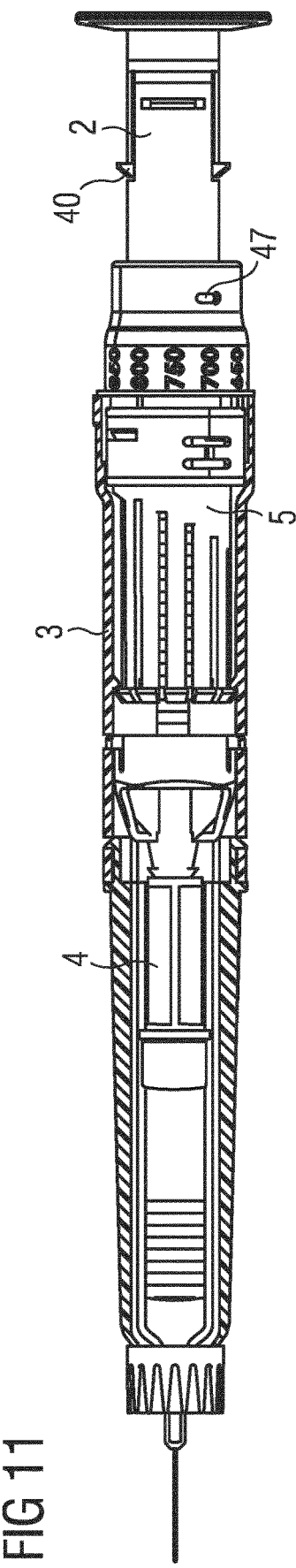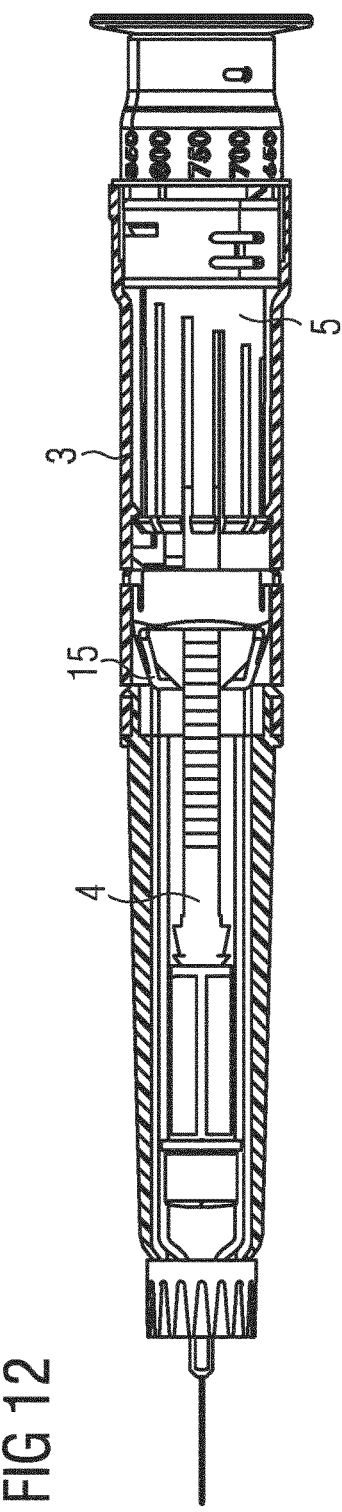

ASSEMBLY FOR A MEDICATION DELIVERY DEVICE AND MEDICATION DELIVERY DEVICE

BACKGROUND OF THE INVENTION

Field of the Invention

The present invention relates to an assembly for a medication delivery device. The present invention further relates to a medication delivery device. In particular, the invention relates to single-shot variable-dose medication delivery device.

In a single-shot variable-dose medication delivery device a dose may be displaced with respect to a body of the device in a distal direction by a piston rod. Thereby, the user settable dose of a medication may be expelled from the device. After delivery of the single dose, the device may be locked for preventing a further dose setting or dose delivery operation.

SUMMARY OF THE INVENTION

It is an object of the present invention to provide an assembly for a medication delivery device having improved properties, e.g., increased user comfort, increased safety, lower error-proneness and/or reduced manufacturing costs. Furthermore, it is an object of the invention to provide a piston rod, also commonly referred to as a plunger, for an improved medication delivery device.

This object may be achieved by the subject matter described herein.

One aspect relates to an assembly for a medication delivery device.

The assembly is configured to perform a dose setting operation. The assembly comprises a dose setting sleeve and a drive sleeve. The assembly further comprises a piston rod and a body. The dose setting sleeve is adapted and arranged to be rotated with respect to the body for setting the dose of the medication. The drive sleeve is configured such that the piston rod is pushed in a distal direction relative to the body by the drive sleeve when the drive sleeve moves in the distal direction relative to the body. The dose setting sleeve comprises a first dosing track having a first length and defining a first size of a dose and at least a second dosing track having a second length and defining a second size of a dose, wherein the first length is different from the second length and the first size is different from the second size. The drive sleeve comprises an engagement feature configured to engage with one of the dosing tracks. The assembly is configured such that the dose setting operation comprises a first step wherein the engagement feature is aligned with one of the tracks and a second step wherein the engagement feature is moved along the track.

Accordingly, both of the dosing tracks and the engagement feature are arranged on sleeves which are movable relative to the body, i.e., the drive sleeve and the dose setting sleeve. The assembly may be configured such that the dose setting sleeve has to be rotated relative to the body to set a dose and that the drive sleeve has to be moved axially relative to the body to dispense the dose. Thereby, the security is increased and the danger of an accidental misuse can be reduced as it is ensured that two separate components have to be operated by a user for dose setting and dose dispensing.

The dose setting operation may be defined as an operation wherein the device or the assembly is prepared to dispense a dose of defined size wherein the size of said dose is determined during the dose setting operation.

The dosing tracks may allow to guide a movement of the drive sleeve. Thereby, the stability of the device may be improved. In particular, as the engagement feature is engaged with one of the dosing tracks during the second step of the dose setting operation, the danger of damaging the assembly, for example, causing the set dose to be changed, due to an impact during the dose setting operation is significantly reduced. Such an impact may be caused, for example, by a fall, i.e., when a user drops the medication delivery device comprising the assembly. Accordingly, the assembly provides an increased stability and prevents damaging the device due to misuse.

Moreover, the dosing tracks may be configured to ensure that only discrete doses can be set. Thereby, the dose setting operation can be facilitated for the user. In particular, users having impaired vision or reduced dexterity require a device that is easy to operate. The design of the assembly comprising dosing track corresponding to discrete doses of a medication may help the user to set the correct dose. For example, the assembly may be configured to enable the user to set a discrete dose by providing audible counting clicks so that the user does not have to refer to a dosing scale. Accordingly, the assembly may provide an improved usability.

The assembly may be adapted and arranged to be integrated/to be used in the medication delivery device. This means that the assembly may provide specific structural and functional features making the assembly suitable for the medication delivery device. The medication delivery device may be a pen-type device, e.g., a pen-type injector or a pen-type pre-filled syringe.

The medication delivery device may be adapted and arranged to dispense a dose, in particular exactly one dose, i.e., a single dose, of a medication. The device may be a single-shot or single-use device. The medication may be a fluid. The single dose of the medication may be chosen or set by a user. The single dose of medication may, thus, be variable. After delivery of the single dose of the medication, the medication delivery device may be discarded. In particular, further use of the device for setting and dispensing a further dose of the device may be impossible.

The dose setting sleeve may be a component that is operated by a user either directly or indirectly to set a dose. The dose setting sleeve may be adapted and arranged to be rotated with respect to a body for setting the dose of the medication. The dose setting sleeve may be gripped for being rotated by the user. The dose setting sleeve may be tubular.

The drive sleeve may be a component that is operated by a user either directly or indirectly for delivering a dose. The drive sleeve may also be operated by a user either directly or indirectly for setting a dose. In particular, the drive sleeve may be moved in a proximal direction with respect to the body or the dose setting sleeve in a second step of the dose setting operation. The drive sleeve may be fixed to an end cap of the assembly. The end cap may be configured to be pressed by a user for delivering the dose. The drive sleeve may be non-releasably fixed to the end cap by fixing elements. Alternatively, the drive sleeve and the end cap may be unitarily formed. The drive sleeve may interact directly with a piston rod of the assembly. In particular, the drive sleeve may be configured such that the piston rod is pushed in a distal direction by the drive sleeve when the drive sleeve moves in the distal direction.

The term "distal" or "distal end" refers to that end of the device or a component that is closest to a dispensing end of the device. The term "proximal" or "proximal end" refers to that end of the device or a component that is furthest away from the dispensing end of the device. The term "distal direction" refers to the direction from the proximal end to the distal end of the device or a component. The term "proximal direction" refers to the opposite direction, i.e., the direction from the distal end to the proximal end.

The dosing tracks may be adapted and arranged to receive the engagement feature. The dosing tracks may be grooves or slots. The dosing tracks may be configured to guide a movement of the drive sleeve by constraining the movement of the engagement feature.

The length of a dosing track may correspond to the distance by which the piston rod is displaced in a dose dispensing operation when the engagement feature has previously been received in the dosing track. The length of a dosing track may correspond to the distance by which a dose is displaced during the dose dispensing operation when the engagement feature has previously been received in the dosing track. The dosing tracks may define discrete doses that a settable by the assembly.

The engagement feature may be any element suitable to be received and guided in a track. For example, the engagement feature may be a protrusion. The engagement feature may be a follower. In particular, the engagement feature may comprise two followers.

Each of the first step and the second step of the dose setting operation may be initiated by a manual action performed by the user. For example, the first step may be initiated by the user rotating the dose setting sleeve which comprises the dosing tracks. The second step may be initiated by the user pulling the drive sleeve in the proximal direction.

The dose setting sleeve may be rotated relative to the drive sleeve during the first step of the dose setting operation. Thereby, the relative radial position of the dosing tracks with respect to the engagement feature may be amended as the dosing tracks are arranged on the dose setting sleeve and the engagement feature is arranged on the drive sleeve.

The drive sleeve may be moved purely linear relative to the dose setting sleeve during the second step of the dose setting operation. In particular, the drive sleeve may be moved purely linear in the proximal direction relative to the dose setting sleeve during the second step of the dose setting operation. Due to the relative movement of the drive sleeve with respect to the dose setting sleeves, the engagement feature may be moved along one of the dosing tracks.

According to one embodiment, the assembly may be configured such that each of the first step and the second step of the dose setting operation is initiated by a user-operated action. In particular, the assembly may comprise a body, wherein the assembly is configured such that the first step of the dose setting operation is initiated by a user rotating the dose setting sleeve relative to the body, and the second step of the dose setting operation is initiated by a user pulling the drive sleeve relative to the body in the proximal direction. The body may be designed to enable a safe and comfortable handling of the medication delivery device. The body may be configured to house, fix, protect and guide inner components of the medication delivery device, e.g., a piston rod, a dose setting sleeve and/or a drive sleeve. Preferably, the body limits or prevents the exposure of the inner components and/or the medication to contaminants such as liquid, dirt or dust. The body may be a unitary or multipart component.

According to one embodiment, the assembly may be configured such that the second step of the dose setting operation is prevented if the engagement feature is not aligned with one of the dosing tracks. In other words, the second step can only be initiated if the engagement feature is aligned with one of the dosing tracks. Thereby, it may be ensured that only discrete dose sizes can be set wherein the dose sizes are defined by the lengths of the dosing tracks. If the engagement feature is not aligned with a dosing track and the user tries to pull the drive sleeve in the proximal direction, a movement of the drive sleeve may be blocked by the engagement feature abutting the dose setting sleeve.

According to one embodiment, the assembly may be configured to perform a dose dispensing operation wherein a dose of a medication is dispensed from the medication delivery device. The assembly may be configured such that, during the first step of the dose setting operation, a size of the dose which is dispensed in the dose dispensing operation is selected by aligning the engagement feature with one of the tracks, and the assembly may be configured such that, during the second step of the dose setting operation, the assembly is prepared to dispense a dose of the size selected in the first step by moving the drive sleeve relative to the dose setting sleeve by a distance corresponding to length of the track to which the engagement feature has been aligned in the first step. In other words, the first step may serve the purpose to select the dose, i.e., to determine the size of the dose to be delivered later. The second step may serve the purpose to actually set the dose, i.e., to prepare the device for dispensing a dose of the previously selected size. By designing the assembly such that selecting and setting are performed in two separate steps, it can be ensured that, during the setting of the dose, a previously selected dose size cannot be amended. Thereby, the safety can be improved.

In particular, during the second step of the dose setting operation, a rotation of the dose setting sleeve relative to the drive sleeve may be prevented by the engagement of the engagement feature with one of the tracks. Thus, it may be prevented to amend the pre-selected dose during the second step.

According to one embodiment, the dose setting sleeve may comprise a third track having a third length and defining a third size of a dose, wherein the third length is different from the first length and the second length and the third size is different from the first size and the second size. The dose setting sleeve may comprise more than three dosing tracks.

According to one embodiment, the assembly may comprise a piston rod and a body, wherein the piston rod is adapted and arranged to be linearly moved in a distal direction with respect to the body for dispensing the medication, and wherein the drive sleeve is mechanically engaged with the piston rod such that a linear movement of the drive sleeve relative to the piston rod in a proximal direction is enabled and such that a linear movement of the drive sleeve relative to the piston rod in a distal direction is prevented. In particular, the drive sleeve and the piston rod may be mechanically engaged by a ratchet arm of the drive sleeve engaging ratchet teeth of the piston rod. The ratchet arm and the ratchet teeth may be adapted and arranged to enable a movement of the piston rod in the proximal direction relative to the drive sleeve and to prevent a movement of the piston rod in the distal direction relative to the drive sleeve.

The assembly may comprise a deflectable feature, wherein the assembly comprises a first stop face, wherein the assembly is configured to be transferred into a locked-out state by the deflectable feature overriding the first stop face, wherein in the locked-out state, any movement of the drive sleeve relative to the body is prevented, and wherein the assembly is configured such that, before setting a dose for the first time, the piston rod is arranged such that the piston rod prevents a deflection of the deflectable feature, thereby preventing the deflectable feature from overriding the first stop face.

The deflectable feature may be arranged on the drive sleeve.

The piston rod may comprise a section having a maximum radial extension, wherein the section having the maximum radial extension is aligned with the deflectable feature before a dose is set for the first time, thereby preventing the deflection of the deflectable feature.

The assembly may be configured such that the drive sleeve is moved in the proximal direction relative to the piston rod for setting a dose, thereby moving the section having the maximum radial extension away from the deflectable feature and, thus, allowing a deflection of the deflectable feature.

According to one embodiment, the assembly may be configured to perform a priming operation wherein a priming dose is dispensed from the device. The priming operation may have to be carried out before a dose setting operation can be performed for the first time. The priming operation may ensure that any tolerances due to manufacturing or assembling are removed. For example, a gap between the piston rod and the dose may be removed during the priming operation. Another possible function of the priming operation could be to remove any air bubbles in a syringe or a cartridge comprising the medication. In this case the device must be oriented needle upwards prior to conducting the priming stroke. The piston rod may be moved in the distal direction relative to the body during the priming operation.

The dose setting sleeve may comprise a priming track having a length which is shorter than the length of the dosing tracks of the dose setting sleeve wherein the priming track defines a size of a priming dose which has to be dispensed before a dose setting operation can be performed for the first time. The length of the priming track may correspond to the distance by which the piston rod is displaced during the priming operation. At the end of the priming operation, the engagement feature may be disengaged from the priming track. In an alternative design, the priming track may have the same length as one of the dosing tracks.

The device may be configured such that the engagement feature cannot re-enter the priming track after it has been disengaged from the priming track. For this purpose, the end of the priming track may be formed with a "one-way" feature. For example, the engagement feature may comprise a flexible protrusions and a bump or a detent may be formed as the one-way feature at the distal end of the priming track. The one-way feature may be arranged and designed to prevent the engagement feature from re-entering the priming track.

According to one embodiment, the priming operation may consist of a single manually-operated step. Said manually-operated step may be pushing the drive sleeve in the distal direction by a priming distance. Thus, the priming operation can easily be performed by any user, even by users suffering from impaired vision and/or reduced dexterity.

The assembly may be configured such that the user cannot avoid or forget priming as it is not possible to initiate a dose setting operation, e.g., by rotating the dose setting sleeve, until priming is completed. Thus, it may not be possible to forget to prime as an unprimed device cannot proceed to the next step.

According to one embodiment, the assembly may be configured such that, during the priming operation, the drive sleeve is moved relative to the dose setting sleeve either purely linear or helical in the distal direction.

If the drive sleeve is moved helical relative to the dose setting sleeve during the priming operation, the priming operation may not be a separate manually-operated operation. Instead, in this case, the priming operation may be performed automatically if a user performs the first step of a dose setting operation, i.e., if a user rotates the dose setting sleeve relative to the drive sleeve. Thereby, the number of user operated steps may be reduced, thus improving the usability of the device. The assembly is configured such that the user cannot avoid or forget priming as the priming operation is performed "automatically", i.e., without the user being aware of it, as a part of the first step of the dose setting operation. As discussed above, even if the priming operation is a separate manually-operated operation, the device may be configured such that it is still not possible to forget to prime as a dose setting operation cannot be initiated in an unprimed device before priming.

A helical priming track may ensure that the dose setting sleeve can be rotated relative to the drive sleeve only in one rotational direction. It may not be possible to pull the drive sleeve in the proximal direction as long as the engagement feature is in the helical priming track.

The assembly may comprise a longitudinal axis. The longitudinal axis may be defined by a linear connection of a dispensing end of the device and an end opposite of the dispensing end. The longitudinal axis may be a symmetry axis of the device. The engagement feature may be a protrusion extending from the drive sleeve in a radial direction away from the longitudinal axis, wherein the tracks on the dose setting sleeve are formed by grooves or slots in the dose setting sleeve. A protrusion and slots or grooves configured to receive said protrusion may provide a simple and compact mechanism which ensures a good mechanical engagement and which is not prone to errors.

The assembly may have an unprimed state and a primed state, wherein the assembly is configured to be transferred from its unprimed state to its primed state by performing a priming operation, wherein the dose setting sleeve has to be rotated relative to the drive sleeve for setting a dose of a medication, wherein the drive sleeve is configured to move the piston rod in a distal direction relative to the body for dispensing the dose, wherein a rotation of the dose setting sleeve relative to the drive sleeve is prevented by a mechanical engagement of the drive sleeve and the dose setting sleeve in the unprimed state of the assembly, and wherein the mechanical engagement of the drive sleeve and the dose setting sleeve is released during the priming operation.

According to one embodiment, the first dosing track and the dosing second track may be parallel to the longitudinal axis. In other word, the dosing tracks may be linear. The dose setting sleeve may comprise further dosing tracks which may also be linear and which may differ from the first and the second dosing track in their length. Linear dosing tracks may provide a simple mechanism to guide a linear movement of the drive sleeve.

According to a further aspect, a medication delivery device is described. The medication delivery device may comprise the previously described assembly. The assembly may be integrated in the device or may be part of the device. The device may be a single-shot variable-dose device. The device may be supplied to the user in an unprimed state. Before the device is in a condition for setting the single dose of the medication, the user may have to prime the device.

After delivery of the single dose of the medication, the device may be locked such that a further dose setting and dose delivery operation may be prevented. In this way, a user-friendly and safe device is provided which has a low number of components.

The medication delivery device may comprises a cartridge comprising a medication which is dispensed in a dose delivery operation by the assembly. Alternatively, the medication delivery device may be a syringe comprising a medication which is dispensed in a dose delivery operation by the assembly.

In the following text, a set of advantageous aspects is described. The aspects are numbered to facilitate referencing features of one aspect in other aspects. Features from the aspects are not only relevant in connection with the specific aspects they relate to but are also of relevance on their own.

The following aspects relate to a prime lock which ensures that a priming operation has to be performed before a dose setting operation and a dose delivery operation can be performed. Thereby, a high dose accuracy can be ensured as any assembly tolerances and/or any air bubble can be removed by performing the priming operation.

The aspects discussed in the following refer to embodiments wherein the prime lock which ensures that the priming operation has to be performed is provided by the dose setting sleeve and the drive sleeve. Thereby, the object is solved to provide an assembly for a medication delivery device with a prime lock which requires only a minimal number of components. In particular, the dose setting sleeve and the drive sleeve may be required for a dose dispensing mechanism anyway such that the prime lock does not increase the number of components.

The aspects 1 to 10 relate to an embodiment wherein the priming operation is user-operated and wherein the priming operation is a separate operation from the dose setting operation. The priming operation may be a "push-to-prime" operation wherein a user has to move the drive sleeve axially for the priming operation. The aspects 11 to 15 relate to an embodiment wherein the priming operation can occur during the first dose setting operation. The user action of rotating the dose setting sleeve can pull the drive sleeve, and thereby the piston rod, in the distal direction. Accordingly, the priming step can be completed as a part of a first step of setting a dose. This provides the advantage of a reduced number of user-operated steps.

1. Assembly for a medication delivery device,
   wherein the assembly has an unprimed state and a primed state,
   wherein the assembly is configured to be transferred from its unprimed state to its primed state by performing a priming operation,
   wherein the assembly comprises a dose setting sleeve, a drive sleeve, a piston rod and a body,
   wherein the dose setting sleeve has to be rotated relative to the drive sleeve for setting a dose of a medication,
   wherein the drive sleeve is configured to move the piston rod in a distal direction relative to the body for dispensing the dose,
   wherein a rotation of the dose setting sleeve relative to the drive sleeve is prevented by a mechanical engagement of the drive sleeve and the dose setting sleeve in the unprimed state of the assembly, and
   wherein the mechanical engagement of the drive sleeve and the dose setting sleeve is released during the priming operation.

2. Assembly according to the preceding aspect,
   wherein, during the priming operation, a priming dose is dispensed from the device, and
   wherein the priming operation has to be performed before a dose can be set for the first time.

3. Assembly according to one of the preceding aspects,
   wherein the assembly is configured such that, during the priming operation, the drive sleeve is moved relative to the dose setting sleeve purely linear in the distal direction.

4. Assembly according to one of the preceding aspects,
   wherein the drive sleeve comprises an engagement feature,
   wherein the dose setting sleeve comprises a priming track,
   wherein, in the unprimed state of the assembly, the drive sleeve and dose setting sleeve are mechanically engaged by the engagement feature being arranged in the priming track.

5. Assembly according to the preceding aspect,
   wherein the priming track is configured to guide a movement of the drive sleeve relative to the dose setting sleeve during the priming operation.

6. Assembly according to aspect 4 or 5,
   wherein the dose setting sleeve comprises one or more dosing tracks which are parallel to the priming track,
   wherein the assembly is configured such that the engagement feature of the drive sleeve engages one of the dosing tracks for setting a dose of the medication.

7. Assembly according to the preceding aspect,
   wherein the one or more dosing tracks are longer than the priming track. In an alternative embodiment the priming track may have the same length as one of the dosing tracks. The device may be configured such that the engagement feature cannot re-enter the priming track after it has been disengaged from the priming track. For this purpose, the end of the priming track may be formed with a "one-way" feature. For example, the engagement feature may comprise a flexible protrusions and a bump or a detent may be formed as the one-way feature at the distal end of the priming track. The one-way feature may be arranged and designed to prevent the engagement feature from re-entering the priming track.

8. Assembly according to one of aspects 6 or 7,
   wherein the length of the priming track corresponds to the distance by which the piston rod is displaced during the priming operation, and
   wherein the length of a dosing track corresponds to the distance by which the piston rod is displaced when a dose is dispensed from the device, wherein the engagement feature has been engaged with said dosing track in a dose setting operation performed before dispensing the dose.

9. Assembly according to one of the aspects 4 to 8,
   wherein the assembly comprises a longitudinal axis, and
   wherein the priming track is parallel to the longitudinal axis.

10. Assembly according to one of the preceding aspects,
    wherein the dose setting sleeve is enabled to rotate relative to the drive sleeve in the primed state of the assembly.

11. Assembly for a medication delivery device,
    wherein the assembly has an unprimed state and a primed state, wherein the assembly is configured to be transferred from its unprimed state to its primed state by performing a priming operation,
    wherein the assembly comprises a dose setting sleeve, a drive sleeve, a piston rod and a body,
    wherein the dose setting sleeve has to be rotated relative to the drive sleeve for setting a dose of the medication, wherein the drive sleeve is configured to move the piston rod in a distal direction relative to the body for dispensing the dose, wherein the assembly is configured such that, when the dose setting sleeve is rotated relative to the drive sleeve for the first time, the priming operation is performed.

12. Assembly according to the preceding aspect, wherein the dose setting sleeve comprises a priming track and one or more dosing tracks, wherein the drive sleeve comprises an engagement feature configured to engage with one of the priming track and the one or more dosing tracks, wherein the assembly is configured such a dose setting operation comprises a first step wherein the engagement feature is aligned with one of the dosing tracks by rotating the dose setting sleeve relative to the drive sleeve and a second step wherein the engagement feature is moved along the dosing track to which it has been aligned in the first step, wherein the assembly is configured such that, when a dose setting operation is performed for the first time, the priming operation is performed during the first step of the dose setting operation.

13. Assembly according to the preceding aspect, wherein the priming track is helical.

14. Assembly according to one of the aspects 12 or 13, wherein the engagement feature is arranged in the priming track in the unprimed state.

15. Assembly according to one of the aspects 12 to 14, wherein the assembly is configured such that the engagement feature is disengaged from the priming track when the dose setting sleeve is rotated relative to the drive sleeve for the first time.

16. Medication delivery device comprising an assembly according to one of the preceding aspects wherein the medication delivery device is a variable-dose, single-use device.

17. Medication delivery device according to the preceding aspect, wherein either the medication delivery device comprises a cartridge comprising a medication which is dispensed in a dose delivery operation by the assembly or the medication delivery device is a syringe comprising a medication which is dispensed in a dose delivery operation by the assembly.

In the following text, another set of advantageous aspects is described. The aspects are numbered to facilitate referencing features of one aspect in other aspects. Features from the aspects are not only relevant in connection with the specific aspects they relate to but are also of relevance on their own.

The aspects discussed in the following refer to embodiments wherein the assembly is configured to prevent an accidental lock-out of the assembly before a dose setting operation has been performed. The lock-out may correspond to a configuration wherein no further operation of the assembly is possible, e.g., because some of the components of the assembly can no longer be moved relative to each other. The assembly may be designed to be locked-out after delivering a dose. However, it should be ensured that an accidental lockout before delivering a dose is prevented. Thus, the aspects discussed in the following may solve the object to improve the usability of the assembly by providing a simple mechanism that prevents an accidental lock-out. The mechanism may require only a minimal number of components.

1. Assembly for a medication delivery device, wherein the assembly comprises a piston rod and a body, wherein the assembly comprises a drive sleeve configured to move the piston rod in the distal direction for dispensing a dose, wherein the assembly comprises a deflectable feature, wherein the assembly comprises a first stop face, wherein the assembly is configured to be transferred into a locked-out state by the deflectable feature overriding the first stop face, wherein in the locked-out state, any movement of the drive sleeve relative to the body is prevented, and wherein the assembly is configured such that, before setting a dose for the first time, the piston rod is arranged such that the piston rod prevents a deflection of the deflectable feature, thereby preventing the deflectable feature from overriding the first stop face.

2. Assembly according to the preceding aspect, wherein the deflectable feature is arranged on the drive sleeve.

3. Assembly according to one of the preceding aspects, wherein the piston rod comprises a section having a maximum radial extension, wherein the section having the maximum radial extension is aligned with the deflectable feature before a dose is set for the first time, thereby preventing the deflection of the deflectable feature.

4. Assembly according to the preceding aspect, wherein the assembly is configured such that the drive sleeve is moved in the proximal direction relative to the piston rod for setting a dose, thereby moving the section having the maximum radial extension away from the deflectable feature and, thus, allowing a deflection of the deflectable feature.

5. Assembly according to one of the preceding aspects, wherein the assembly comprises a second stop face, wherein the assembly is configured such that the deflectable feature overrides the first stop face when dispensing a previously set dose, and wherein the assembly is configured such that the deflectable feature abuts the second stop face after overriding the first stop face.

6. Assembly according to the preceding aspect, wherein the second stop face is adapted and arranged to prevent a movement of the drive sleeve in the proximal direction relative to the body.

7. Assembly according to one of the aspects 7 or 8, wherein the assembly is configured such that no dose can be set when the drive sleeve abuts the second stop face.

8. Assembly according to one of the preceding aspects, wherein the assembly comprises a dose setting sleeve configured to be rotated relative to the body for setting a dose, wherein the dose setting sleeve comprises the first stop face.

9. Assembly according to the preceding aspect, wherein the assembly has an unprimed state and a primed state, wherein the assembly is configured to be transferred from its unprimed state to its primed state by performing a priming operation, wherein the assembly is configured such that the deflectable feature is brought into abutment with the first stop face during the priming operation.

10. Assembly according to the preceding aspect, wherein the assembly is configured such that, during the priming operation, the piston rod is displaced in the distal direction by a distance which is identical to the distance of the deflectable feature to the first stop face in the unprimed state of the assembly.

11. Assembly according to one of the aspects 8 or 9,
wherein the assembly is configured such that the priming operation has to be performed before setting a dose for the first time.

12. Assembly according to one of the preceding aspects,
wherein the assembly is configured such that a distal movement of the drive sleeve relative to the body is prevented when the deflectable feature abuts the first stop face and the piston rod prevents a deflection of the deflectable feature.

13. Assembly according to the preceding aspect,
wherein the first stop face is shaped to enable the deflectable feature to override the first stop face, and
wherein the deflectable feature is adapted and arranged such that it is enabled to override the first stop face when the deflectable feature deflects inwardly.

14. Medication delivery device comprising an assembly according to one of the preceding aspects wherein the medication delivery device is a variable-dose, single-use device.

15. Medication delivery device according to the preceding aspect,
wherein either the medication delivery device comprises a cartridge comprising a medication which is dispensed in a dose delivery operation by the assembly or the medication delivery device is a syringe comprising a medication which is dispensed in a dose delivery operation by the assembly.

Features which are described herein above and below in conjunction with different aspects or embodiments, may also apply for other aspects and embodiments. Further aspects, features and advantages of the present invention will be apparent from the following description of preferred embodiments with reference to the accompanying drawings.

BRIEF DESCRIPTION OF THE DRAWINGS

FIG. 1 schematically shows a perspective view of a medication delivery device.

FIG. 2 schematically shows a cross-sectional view of the medication delivery device.

FIG. 9 schematically shows a sectional side view of the medication delivery as supplied from the manufacturer.

FIG. 10 schematically shows a sectional side view of the medication delivery in a primed state.

FIG. 11 schematically shows a sectional side view of the medication delivery after a dose has been set.

FIG. 12 schematically shows a sectional side view of the medication delivery after the dose has been dispensed.

DETAILED DESCRIPTION OF THE INVENTION

Figure 3:
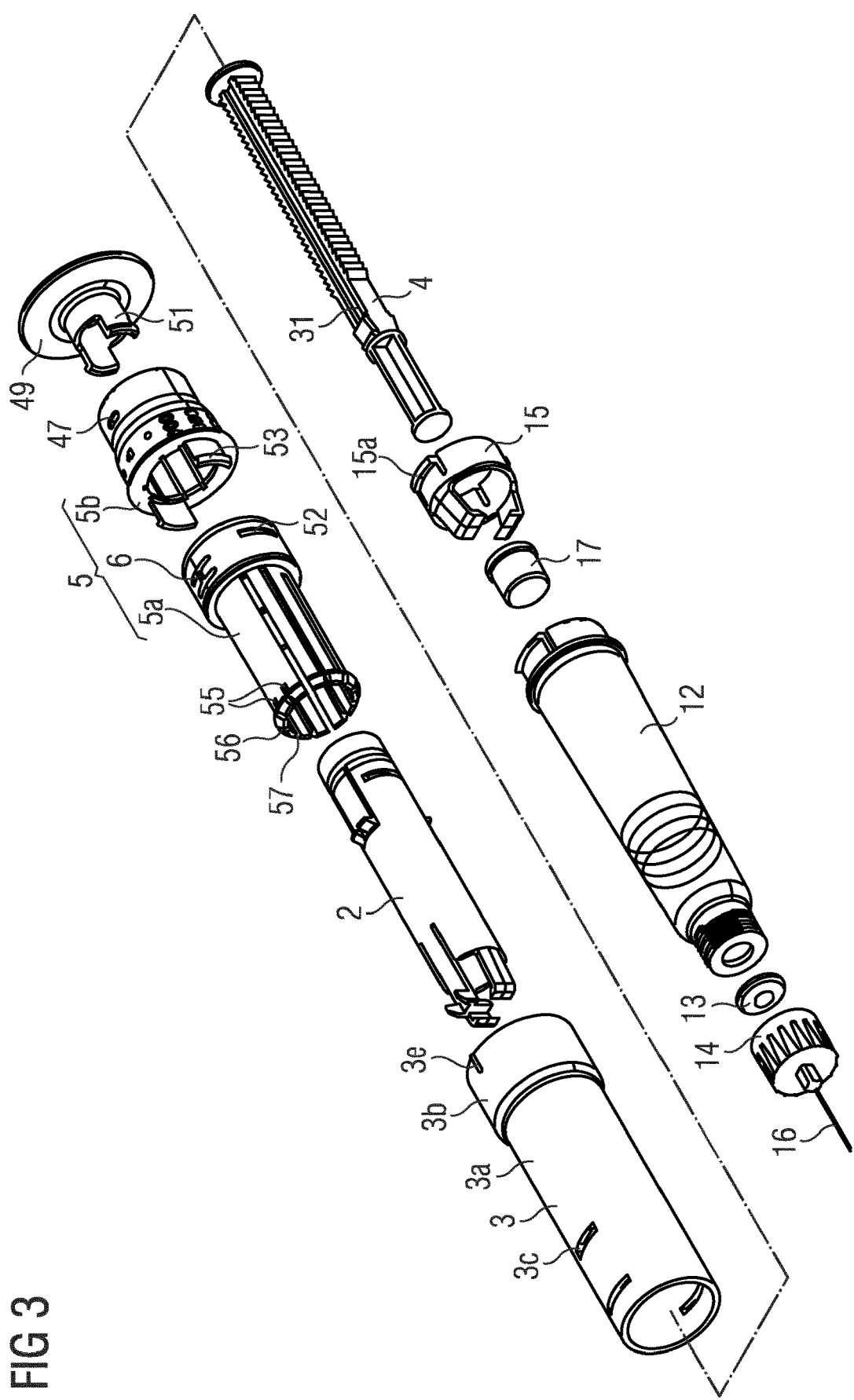
FIG. 3 schematically shows an exploded view of the medication delivery device.

Like elements, elements of the same kind and identically acting elements may be provided with the same reference numerals in the figures.

FIG. 1 shows a perspective view of a medication delivery device 1. FIG. 2 shows a cross-sectional view of the medication delivery device 1. FIG. 3 shows an exploded view of the medication delivery device 1.

The medication delivery device 1 is adapted and arranged to retain a medication 10, preferably one dose of the medication. The medication 10 is preferably a liquid. The device 1 may be a one-shot variable dose device. This means that the device 1 may be intended for a single use, i.e., for dispensing only one dose of the medication 10. After delivery of said dose of the medication 10, the device 1 may be discarded. The size of said dose of medication 10 may be settable by a user, i.e., it is a variable dose. Accordingly, the device 1 must contain sufficient medication 10 for setting and dispensing a maximum settable dose from the device, e.g., 900 units. For the case that less than the maximum settable dose is set and dispensed, medication 10 will be left over in the device. The remaining medication 10 will be discarded together with the device 1 after delivery of the set dose of the medication 10. Moreover, the device 1 may be configured such that a minimum possible dose of the medication 10, e.g., 500 units, has to be set.

The medication delivery device 1 comprises a body 3. The body 3 may be designed to enable a safe and comfortable handling of the medication delivery device 1. The body 3 may be configured to house, fix, protect and guide inner components of the medication delivery device 1, e.g., a piston rod 4, a dose setting sleeve 5, and/or a drive sleeve 2 which are described below in detail. Preferably, the body 3 limits or prevents the exposure of the inner components and/or the medication 10 to contaminants such as liquid, dirt or dust. The body 3 may be a unitary or multipart component. The body 3 may comprise a tubular or cylindrical shape. Alternatively, the body 3 may comprise a non-tubular shape.

The body 3 comprises a distal main section 3a and a proximal end section 3b which succeeds the distal main section in the proximal direction. Each of the distal main section 3a and the proximal end section 3b is tubular wherein the diameter of the proximal end section 3b is wider than the diameter of the distal main section 3a.

The body 3 comprises an opening 3c configured to receive a lug 15a of a non-return ratchet 15, thereby fixing the non-return ratchet 15 to the body 3, as will be described later. The opening 3c is arranged in the distal main section 3a of the body 3.

The body 3 comprises a plurality of grooves 3d (see FIGS. 9 and 10) arranged at an inner surface of the body 3. The grooves 3d extend from a proximal end of the body 3 in an axial direction through the proximal end section 3b. The grooves 3d are not arranged in the distal main section 3a. As will be described later, the grooves 3d are adapted and arranged to mechanically cooperate with a deflectable detent 6 of a dose setting sleeve 5.

The body 3 comprises a marker 3e which is configured to be aligned with symbols 7 arranged on the dose setting sleeve 5 to provide information concerning the currently set dose of the device 1. The marker 3e is an elevation of the tubular body 3. Of course, other kind of markers are also possible, e.g., a colored marking on the body.

The medication delivery device 1 and the body 3 have a distal end 8 and a proximal end 9. The distal end 8 designates that end of the device 1 or a component thereof which is closest to a dispensing end of the medication delivery device 1. The proximal end 9 designates that end of the device 1 or a component thereof which is furthest away from the dispensing end of the medication delivery device 1.

Figure 13:
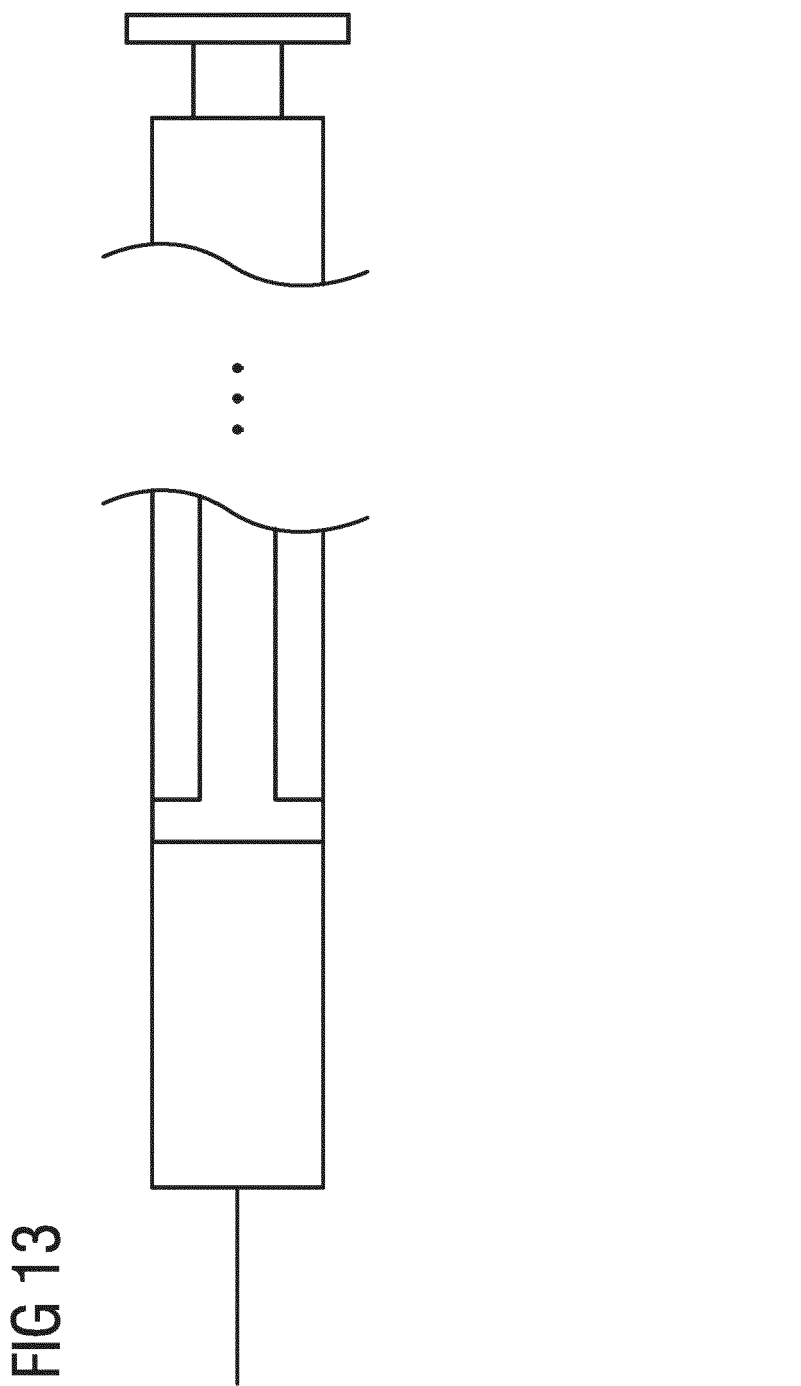
FIG. 13 schematically shows a sectional side view of parts of a medication delivery device according to a second embodiment.

In one embodiment the medication delivery device 1 comprises a cartridge 11 for holding the medication 10. In this case, the cartridge 11 may be retained within a cartridge holder 12. The cartridge holder 12 may be connected, e.g., snap-fitted or screwed to the body 3. The cartridge holder 12 may be configured for stabilizing the cartridge 11 mechanically. Alternatively, the body 3 may be adapted and arranged to house and protect the medication 10. In this case, the medication 10 may be retained directly within the body 3, in particular in a specific section or region, e.g., the most distal region of the body 3. Accordingly, the cartridge 11 for retaining the medication 10 and the cartridge holder 12 may be superfluous. In this embodiment, the medication delivery device 1 is supplied and designed as a pre-filled syringe. In this embodiment, the medication delivery device 1 is supplied and designed as a pre-filled syringe as can be gathered from FIG. 13.

The cartridge 11 or the body 3 may comprise an outlet. The medication 10 can be dispensed from the cartridge 11 or the body 3 through said outlet. A septum 13 may seal the outlet. The septum 13 may be made of an elastically deformable material. The device 1 further comprises a needle assembly 14. The needle assembly 14 may be connected, e.g., screwed, to the distal end of the cartridge holder 12 or the body 3. By means of the needle assembly 14 a needle 16 may be secured to the device 1. The septum 13 may be piercable by the needle 16 for dispensing a dose of the medication 10 via the needle 16 extending through the outlet.

The device 1 comprises a dose 17. The dose 17 may be slidably retained within the cartridge 11 or the body 3 of the device 1. Preferably, the dose 17 comprises a resilient material. The dose 17 may seal the cartridge 11 or the section of the body 3 containing the medication 10 proximally. The dose 17 is movable with respect to the cartridge 11 or the body 3. In particular, axial movement of the piston rod 4 for delivering the set dose may be transferred to the dose 17. Movement of the dose 17 in the distal direction with respect to the body 3 causes the medication 10 to be dispensed from the device 1 through the outlet.

Figure 4:
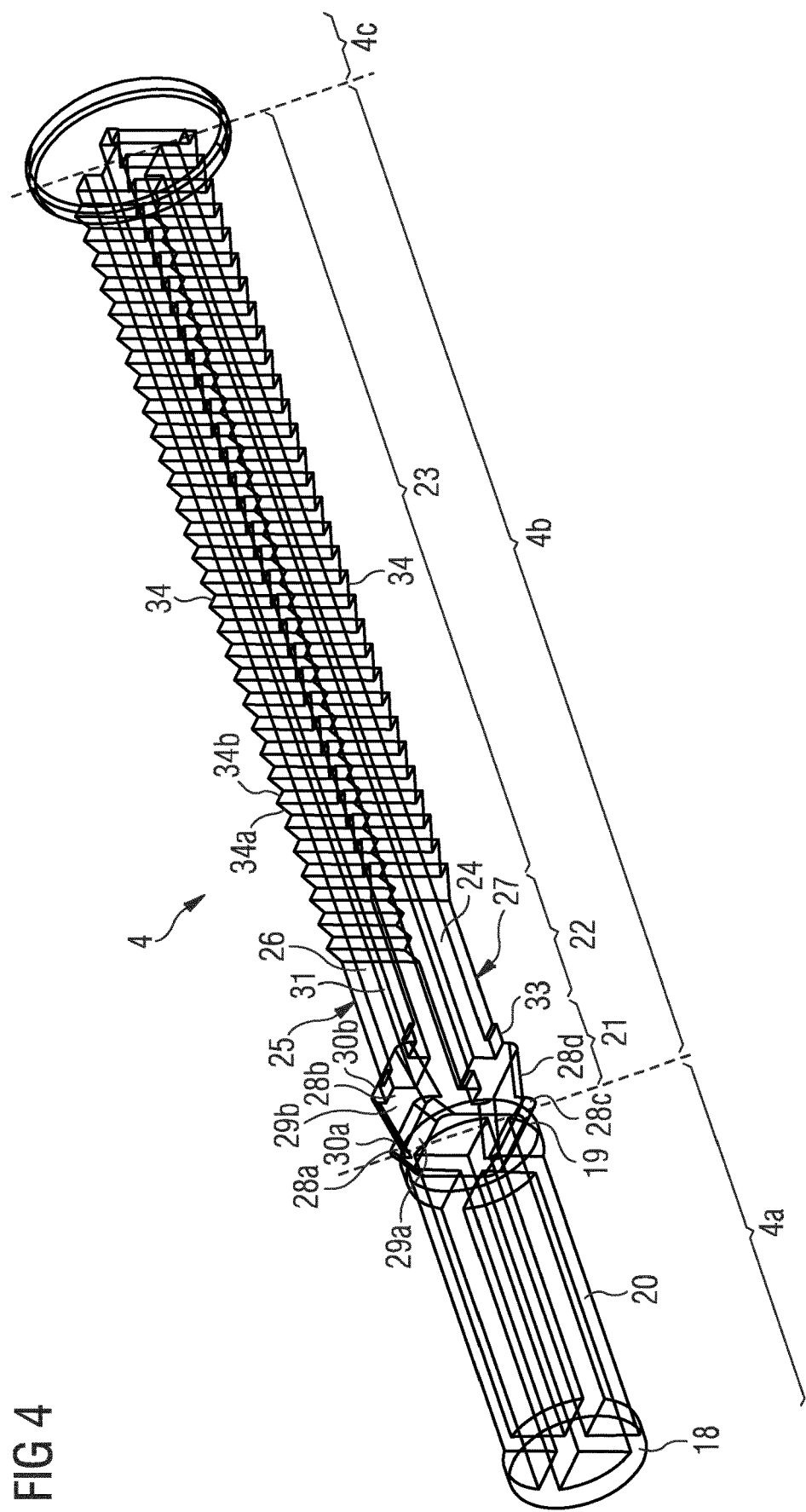
FIG. 4 schematically shows a perspective view of a piston rod of the medication delivery device.

The medication delivery device 1 further comprises the previously mentioned piston rod 4. FIG. 4 shows a perspective view of the piston rod 4. The piston rod 4 may be an injection molded component. The piston rod 4 is adapted and arranged to operate through the body 3 of the device 1. The piston rod 4 is designed to transfer an axial movement through the medication delivery device 1, for example for the purpose of delivering the set dose of the medication 10. The piston rod 4 is axially, in particular distally, movable with respect to the body 3 for delivering the set dose of medication 10. The piston rod 4 is prevented from rotating relative to the body 3. In particular, an engagement of the piston rod 4 with a first claw 15b and a second claw 15d of the non-return ratchet prevents a rotation of the piston rod relative to the body 3. Further, the piston rod 4 is prevented from moving in a proximal direction relative to the body 3. During a dose delivery, the piston rod 4 is moved along a longitudinal axis of the device 1 in the distal direction relative to the body 3. During a dose setting, the piston rod 4 is not moved relative to the body 3. During priming, the piston rod 4 is moved along the longitudinal axis in the distal direction relative to the body 3.

The piston rod 4 comprises a first axial region 4a, a second axial region 4b and a third axial region 4c. The axial regions 4a, 4b, 4c extend along the longitudinal axis of the piston rod 4. The regions pass over into one another. In particular, the piston rod 4 is integrally formed, which means that the piston rod 4 is a one-piece component. A transition area between adjacent regions is indicated by the dashed lines in FIG. 4. The first axial region 4a is the most distal region, i.e., it is arranged closest to a dispensing end of the device 1. The third axial region 4c is the most proximal region, i.e., it is arranged furthest away from the dispensing end. The second axial region 4b is arranged between the first and the third axial region. Each of regions comprises different structures and functions as compared to one another.

The first axial region 4a comprises a distal end 18. The distal end 18 of the first axial region 4a is shaped plate-like. The distal end 18 is adapted and arranged for mechanical cooperation with the previously mentioned dose 17 of the device 1.

The first axial region 4a comprises a plate-like structure 19 arranged at a proximal end of the first axial region 4a. The plate-like structure 19 is disc-shaped. The plate-like structure 19 forms a pre-priming abutment face. The previously mentioned claws 15b, 15d of the non-return ratchet 15 abuts the pre-priming abutment face when the device 1 is in its unprimed state as will be described later.

The first axial region 4a finally comprises a middle section 20 arranged between the distal end 18 and the plate-like structure 19. The middle section 20 is segmented. In particular, it comprises four axially extending segments or struts which extend along the longitudinal axis of the piston rod 4. In a cross-sectional view perpendicular to the longitudinal axis, the middle section 20 is cross-shaped. The distal end of the middle section 20 is terminated by the distal end 18 of the first region 4a. The proximal end of the middle section 20 is terminated by the plate-like structure 19. By means of the segmented middle section 20 of the first region 4a, it is ensured that a wall thickness of a plastic material of the piston rod is relatively constant throughout the piston rod. This in turn ensures that the plastic shrinks evenly throughout. If the middle section 20 was solid and therefore thicker, it would cool more slowly after molding and therefore would shrink more. This would result in visible "sinking" on the surfaces and potentially axial bending, e.g., if one side shrinks more than the other. Furthermore, the material costs are reduced by the design of the middle section 20.

In the proximal direction, the first axial region 4a passes over into the second axial region 4b. The second axial region 4b comprises a distal section 21, a middle section 22 and a proximal section 23 wherein, in the proximal direction, the distal section 21 is succeeded by the middle section 22 and the middle section 22 is succeeded by the proximal section 23.

The second axial region 4b comprises a first face 24, a second face 25, a third face 26 and a fourth face 27 wherein the first and the second face 24, 25 are parallel to each other and perpendicular to the third face 26 and the fourth face 27. The third and the fourth face 26, 27 are parallel to each other. Accordingly, the first face 24 and the second face 25 may be side faces of the second axial region 4b. The third face 26 may be an upper face of the second axial region 4b. The fourth face 27 may be a lower face of the second axial region 4b. Each of the first to fourth face is structured, i.e., each of the faces comprises structures which are explained in detail in the following.

In the distal section 21 of the second axial region 4b, the edges between adjacent faces are rounded.

The second axial region 4b comprises a first priming tooth 28a and a second priming tooth 28b. The non-return ratchet 15 of the device 1 which will be described in more detail later is engaged with the first priming tooth 28a in an unprimed state of the device 1. The first priming tooth 28a and the second priming tooth 28b are arranged subsequently to each other in the distal section of the second axial region 4b. The first and the second priming teeth 28a, 28b are arranged on the third face 26. The second axial region 4b further comprises a third priming tooth 28c which is arranged opposite of the first priming tooth 28a with respect to the longitudinal axis of the device 1 and a fourth priming tooth 28d which is arranged opposite of the second priming tooth 28b with respect to the longitudinal axis, i.e., the third and the fourth priming teeth 28c, 28d are on the fourth face 27 of the piston rod 4. The third and the fourth priming teeth 28c, 28d are also arranged in the distal section 21 of the second axial region 4b. In the following, mostly only the first priming tooth 28a and the second priming tooth 28b will be described. The third and the fourth priming teeth 28c, 28d have an identical structure and serve the identical functions as discussed with respect to the first priming tooth 28a and the second priming tooth 28b.

The first priming tooth 28a has a distal surface 29a which is inclined relative to the longitudinal axis by a first angle. The distal surface 29a is shaped such that the first claws 15b of the non-returned ratchet 15 can slide over the distal surface 29a. The first priming tooth 28a has a proximal surface 30a which is substantially perpendicular to the longitudinal axis. In particular, it is not essential that the proximal surface 30a is exactly perpendicular to the longitudinal axis. For example, it might be sufficient to be almost perpendicular, e.g., by forming an angle in the range of 85° to 90° to the longitudinal axis. Alternatively, it might be beneficial for the proximal surface 30a to be undercut, i.e., to form an angle larger than 90°, in order to provide a stronger engagement with the non-return ratchet. The distal surface 29a of the first priming tooth 28a is confined by the proximal surface 30a of the first priming tooth 28a. The proximal surface 30a of the first priming tooth 28a is adapted and arranged such that the first claw 15b of the non-return ratchet 15 is prevented from sliding over the first priming tooth 28a in the distal direction.

The second priming tooth 28b has a similar shape as the first priming tooth 28a. However, the second priming tooth 28b has a distal surface 29b which is inclined relative to the longitudinal axis by a second angle wherein the second angle is less steep than the first angle. Thus, the second priming tooth 28b has a longer axial extension as the first priming tooth 28a. The second priming tooth 28b also comprises a proximal surface 30b which is perpendicular to the longitudinal axis of the piston rod 4.

However, it is not essential that the angle of the second priming tooth 28b is less steep than the angle of the first priming tooth 28a. In the first priming tooth 28a, the angled face only serves to provide mechanical strength to the proximal face. In the second priming tooth 28b, the angled face is at a shallower angle only because the priming distance is longer than the "mechanical strength angle" needed in the first priming tooth 28a. An advantage of having a shorter first priming tooth 28a is that the piston rod diameter can return to the smaller diameter necessary to insert into the Cartridge inner diameter. It is also acceptable for first priming tooth 28a to have a steeper angle because the claws of the non-return ratchet 15 do not have to travel over this surface.

The first claw 15b of the non-return ratchet 15, which abuts the pre-priming abutment face when the device 1 is in the unprimed state, slides over the first priming tooth 28a and the second priming tooth 28b during the priming operation. In the primed state, the first claw 15b abuts the proximal surface 30b of the second priming tooth 28b.

The first face 24 and the second face 25 are flat, i.e., free from structural elements, in the distal section 21 of the second axial region 4b. When seen in a side view, i.e., along the surface normal of the first or the second face, the first and the second faces 24, 25 have the shape of two subsequent trapezoids corresponding to the priming teeth.

In the middle section 22 of the second axial region 4b, the first and the second faces 24, 25 are also flat, i.e., free from structural elements.

In the middle section 22 of the second axial region 4b, the third and the fourth face 26, 27 each comprise a linear slot 31. In the following, mostly only the slot 31 on the third face 26 is described. The slot on the fourth face 27 has an identical structure and serves the identical functions as discussed with respect to the slot 31 on the third face 26.

The slots 31 are parallel to the longitudinal axis of the device 1, i.e., the slots 31 have the form of a straight line. A distal end of the slot 31 arranged on the third face 26 is confined by the proximal surface 30a of the first priming tooth 28a. The slot 31 extends along the middle section 20 of the second axial region 4b and along the proximal section 23 of the second axial region 4b. As will be described later, the drive sleeve 2 is engaged with the piston rod 4 via a protrusion 32 which is arranged in the slot 31 on the third face 26 and which is guided by the slot 31.

A small step 33 is arranged on each of the third and the fourth face 26, 27 in the middle section 22. The small step 33 is adjacent to the second priming tooth 28b and, respectively, to the fourth priming tooth 28d. The small step 33 is formed on the left and the right side of the slots 31. The step 33 is adapted and arranged such that it creates an audible and tactile feedback of the start of an injection via an interaction with the first and second claws 15b, 15d of the non-return ratchet 15.

As mentioned above, in the proximal section 23 of the second axial region 4b, the slots 31 extends along the third and the fourth face 26, 27 which are flat apart from the slots 31.

The first face 24 and the second face 25 are structured in the proximal section 23 of the second axial region 4b. The second axial region 4b comprises a plurality of ratchet teeth 34 extending from the first face 24 and from the second face 25. The ratchet teeth 34 extend along the whole proximal section 23 of the second axial region 4b. The ratchet teeth 34 are straight. This means that a proximal edge 34a of a respective ratchet tooth 34 extends perpendicular to the longitudinal axis. A distal edge 34b of the respective ratchet tooth 34 is oblique with respect to the longitudinal axis. As will be described later, the ratchet teeth 34 are configured to be engaged with the drive sleeve 2 such that the drive sleeve 2 is enabled to be moved in the proximal direction with respect to the piston rod 4 and such that the drive sleeve 2 is prevented from moving in the distal direction with respect to the piston rod 4.

In the embodiment shown in the figures, the piston rod 4 comprises a plurality of ratchet teeth 34. It is not essential that the ratchet teeth 34 are continuous or are evenly spaced.

The only essential ratchet teeth 34 are those that correspond with the ends of the dosing tracks, i.e., the ratchet teeth 34 which will engage with the ratchet arms 38 when a selected dose is fully set.

In an alternative embodiment, only a single dose may be selectable after priming. In such an embodiment, only a single ratchet tooth 34 is required. This would also have the advantage of a lower friction to pull the drive sleeve 2 during dose setting because there would be no ratchet clicks to overcome and mean that setting of a partial dose is not possible because the ratchet would not engage until dose is fully set.

In the proximal direction, the second axial region 4b passes over into the third axial region 4c. The third axial region 4c is shaped plate-like. The third axial region 4c comprises a radial extension which is greater than a radial extension of the first region 4a or the second region 4b. Thus, the third axial region 4c is the region having a maximum radial extension of the piston rod 4.

In the design of the piston rod 4 as shown in the Figures, the priming teeth 28a, 28b, 28c, 28d and the ratchet teeth 34 are constructed on different faces 24-27 of the square sectioned piston rod 4. Thus, during dispense of medication from the device, the non-return ratchet 15 is not clicking over any teeth. This has the advantage of not adding any friction to the dispensing stroke.

If, after a partial dispense, the user should decide to pull back the end cap 49 in the proximal direction, then the piston rod 4 will be pulled in the proximal direction. As the piston rod 4 is not connected to the cartridge dose 17, no air would be pulled into the cartridge 11 by this action such that no problem arises from this action.

However, in an alternative embodiment, the priming teeth 28a-28d and ratchet teeth 34 may be arranged on the same two opposing faces 26, 27 of the piston rod 4. This means that during dispense the non-return ratchet 15 will be clicking over the ratchet teeth 34. This will create tactile and audible feedback during injection, at cost of a slightly increased friction. However, it also means that if user pulls back the end cap 49 proximally, then the piston rod 4 cannot move proximally due to an engagement of the non-return ratchet 15 with the ratchet teeth 34. The drive sleeve 2 could return to the end of the dosing track, clicking over the ratchet arms 38 as it goes. Thus, in this embodiment, a user could unintentionally dispense a larger dose than perhaps intended if the user pulls the end cap 49 in the proximal direction after having started to dispense a dose and before finishing the dispense.

As discussed above, this potential dosing error does not occur in the embodiment shown in the figures as the teeth 28a-28d and 34 are arranged on different sides. Alternatively, this potential dosing error may also be prevented by implementing a one-way function into the end cap 49, i.e., by providing an end cap 49 that can only be pulled proximally one time, after which it will engage another ratchet so that it can only be pushed distally and not pulled proximally.

Figure 5:
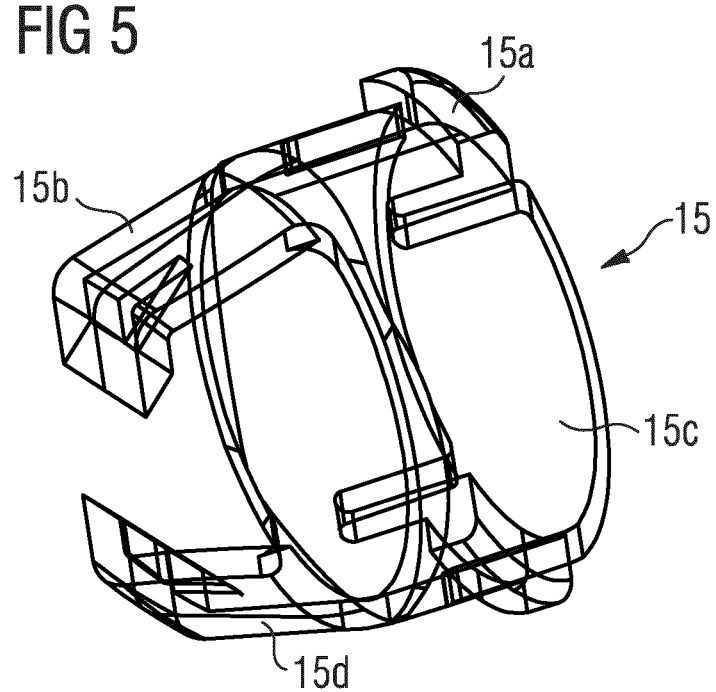
FIG. 5 schematically shows a perspective view of a non-return ratchet of the medication delivery device.

The medication delivery device 1 further comprises the previously mentioned non-return ratchet 15. FIG. 5 shows a perspective view of the non-return ratchet 15.

The non-return ratchet 15 is configured to surround the longitudinal axis of the device 1. The non-return ratchet 15 is configured to encircle the piston rod 4.

The non-return ratchet 15 comprises a ring-shaped main body 15c. The non-return ratchet 15 comprises the first claw 15b which extends from the ring-shaped main body 15c in the distal direction. A proximal end of the first claw 15b is formed at the main body 15c. The first claw 15b has a first section succeeding its proximal end in a distal direction. The first section of the first claw is inclined towards the longitudinal axis. In particular, the first section is inclined towards the longitudinal axis at a small angle in the range of 5° to 45°. The first claw 15b further comprises a second section which succeeds the first section in the distal direction and which is perpendicular to the longitudinal axis. The second section comprises a distal end of the first claw 15b. The distal end of the first claw 15b is configured to engage with the first priming tooth 28a of the piston rod 4. The distal end of the first claw 15b is configured to abut the pre-priming abutment face of the piston rod 4 in the unprimed state. The first claw 15b is further configured to slide along the first and the second priming teeth 28a, 28b during the priming operation.

Further, the non-return ratchet 15 comprises a second claw 15d which has an identical structure as the previously described first claw 15b. The second claw 15d is arranged opposite the first claw 15b with respect to the longitudinal axis. The first claw 15b is configured to engage the first and the second priming teeth 28a, 28b and the second claw 15d is configured to engage the third and the fourth priming teeth 28c, 28d.

The main body 15c of the non-return ratchet 15 further comprises the previously-mentioned lug 15a. The lug 15a extends in the radial direction away from the longitudinal axis of the device 1. The lug 15a is configured to be received in the opening 3c of the body 3. The engagement of the non-return ratchet 15 with the body 3 by the lug 15a being received in the opening 3c fixes the non-return ratchet 15 with respect to the body 3. It is not possible to rotate the non-return ratchet 15 with respect to the body 3. It is also not possible to move the non-return ratchet 15 linearly with respect to the body 3.

Figure 6:
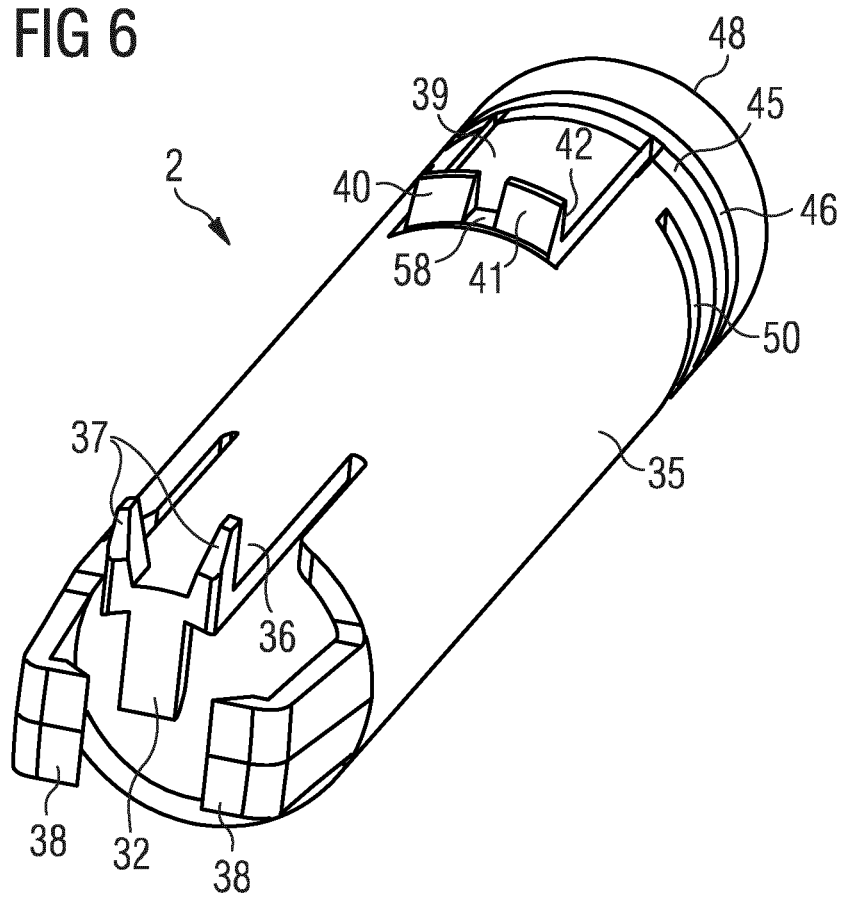
FIG. 6 schematically shows a perspective view of a drive sleeve of the medication delivery device.

The medication delivery device further comprises the previously mentioned drive sleeve 2. FIG. 6 shows a perspective view of the drive sleeve 2.

The drive sleeve 2 is a tubular component. The piston rod 4 is at least partially arranged inside the drive sleeve 2. The drive sleeve 2 and the piston rod 4 are rotationally locked with respect to each other, i.e., it is not possible to rotate the drive sleeve 2 relative to the piston rod 4. The drive sleeve 2 is enabled to be moved in the proximal direction with respect to the piston rod 4 and with respect to the body 3. The drive sleeve 2 is further enabled to be moved in the distal direction with respect to the body 3. The drive sleeve 2 is prevented from being moved in the distal direction with respect to the piston rod 4.

The drive sleeve 2 comprises a tubular main body 35. The inner diameter of the tubular main body 35 is slightly bigger than the maximum radial extension of the piston rod 4. In particular, the inner diameter of the tubular main body 35 is bigger by no more than 5 millimeters, preferable no more than 3 millimeters, than the maximum radial extension of the piston rod 4.

The drive sleeve 2 comprises the previously mentioned protrusion 32. The protrusion 32 is formed at an arm 36 extending from the tubular main body 35 in the distal direction. The protrusion 32 extends from the arm 36 in a radially inward direction. The protrusion 32 is configured to be arranged inside the slot 31 of the piston rod 4. The protrusion 32 being slidably arranged in the slot 31 of the piston rod 4 rotationally locks the piston rod 4 and the drive sleeve 2 to each other.

The drive sleeve 2 further comprises an engagement feature 37. The engagement feature 37 is arranged on the arm 36 extending from the tubular main body 35. The engagement feature 37 extends in a radially outward direction away from the longitudinal axis of the device 1. The engagement feature 37 may be a follower. In particular, the engagement feature 37 may comprise two identical followers arranged parallel to each other. In an alternative design, the engagement feature 37 may comprise only a single follower. The engagement feature 37 is configured to engage with tracks 55, 56, 57 on the dose setting sleeve 5 as will be described later. In particular, during priming, the two followers of the engagement feature 37 are configured to engage with two priming tracks 55 of the dose setting sleeve 5. Further, during a dose setting operation, the two followers of the engagement feature 37 are configured to engage with two of the dosing tracks 56, 57 of the dose setting sleeve 5 wherein the shorter one of said two dosing tracks 56, 57 determines the settable dose. As the engagement feature 37 is engageable via two followers, both followers contribute to the rotational strength against the track side walls.

Moreover, the drive sleeve 2 comprises two ratchet arms 38 configured to engage with the ratchet teeth 34 of the piston rod 4. The ratchet arms 38 extend from the tubular main body 35 of the drive sleeve 2 in the distal direction. One of the ratchet arms 38 is configured to engage with the ratchet teeth 34 on the first face 24 of the piston rod 4 and the other of the ratchet arms 38 is configured to engage with the ratchet teeth 34 on the second face 25 of the piston rod 4.

The drive sleeve 2 further comprises a deflectable feature 39. The deflectable feature 39 is formed in the tubular main body 35. In particular, the deflectable feature 39 is tongue-shaped. The deflectable feature 39 is formed by a U-shaped cutout in the tubular main body 35. The deflectable feature 39 comprises a projection 40. The projection 40 projects in a radial direction away from the longitudinal axis of the device 1. The projection 40 comprises a distal face 41 which is inclined relative to the longitudinal axis and a proximal face 42 which is largely perpendicular to the longitudinal axis, i.e., the proximal face 42 and the longitudinal axis may form an angle in the range of 80° to 100°. It might be advantageous for the projection 40 to be undercut in order to increase the strength of the lock out, i.e., when pulled proximally an undercut ratchet surface will tend to engage more forcefully as it will tend to move radially outwards, rather than slip radially inwards.

As the distal face 41 of the projection 40 is inclined, the projection 40 is enabled to override a first stop face 43 of the dose setting sleeve 5 as will be discussed later. As the proximal face 42 of the projection 40 is perpendicular to the longitudinal axis, the projection 40 is prevented from overriding a second stop face 44 of the dose setting sleeve 5 in the proximal direction as will be discussed later.

The deflectable feature 39 is configured to be deflected radially inward with respect to the tubular main body 35 of the drive sleeve 2. In particular, when an inwardly directed force is applied to the projection 40, the deflectable feature 39 deflects radially inward. The deflectable feature 39 may be elastic. Thus, when said force is no longer applied to the projection 40, the deflectable feature 39 returns to its un-deflected position.

The projection 40 is adapted and arranged such that the third axial region 4c of the piston rod 4 is aligned with the projection 40 in the primed state of the device 1. In the primed state, the piston rod 4 abuts or almost abuts the inner surface of the deflectable feature 39. Thus, the piston rod 4 prevents an inward deflection of the deflectable feature 39 in the primed state.

The projection 40 comprises a slot 58. The slot 58 extends in the axial direction and separates the projection 40 into two teeth. The slot 58 is adapted and arranged to be engaged with a rib 60 of the dose setting sleeve 5 in the unprimed state and with a further rib 59 of the dose setting sleeve 5 in the locked-out state. The engagement of the slot 58 and with the rib 60 or with the further rib 59 prevents a relative rotation of the drive sleeve 2 and dose setting sleeve 5. Thus, it would not be possible for the user to rotate the dose setting sleeve 5 of a locked device relative to the body 3. It is also not possible for the user to rotate the dose setting sleeve 5 relative to the body in an unprimed device.

The drive sleeve 2 may be configured to provide information about the state of the device 1 to a user of the device 1. For this purpose, the drive sleeve 2 may comprise a color-coding. In particular, a first colored ring 45 and a second colored ring 46 may be arranged on the drive sleeve 2. The first colored ring 45 may be blue and the second colored ring 46 may be orange. Of course, different colors are conceivable. Depending on the state of the device, the first colored ring 45, the second colored ring 46 or none of the rings may be visible in a window 47 of the dose setting sleeve 5. If a ring 45, 46 is visible in the window 47 depends on the relative axial position of the drive sleeve 2 comprising the rings 45, 46 with respect to the dose setting sleeve 5 comprising the window 47.

Each of the colored rings may indicate a specific state of the device 1. For example, the first colored ring 45 may be visible in the window 47 when the device 1 is in its primed state, i.e., after a priming operation has been performed and the device 1 is ready for setting a dose. The second colored ring 46 may be visible in the window 47 when the device 1 is in its locked-out state, i.e., after a dose dispensing operation has been finished and a further operation of the device 1 is not possible. In other states of the device 1, none of the rings 45, 46 may be visible in the window 47.

Of course, the coding may be provided in different manners. For example, instead of rings 45, 46, symbols or letters may be arranged on the drive sleeve 2 to provide information about the state of the device 1.

The drive sleeve 2 further comprises an open proximal end 48. In the open proximal end 48, an end cap 49 is inserted. The end cap 49 constitutes a proximal closure of the drive sleeve 2. The end cap 49 comprises a rear disc-shaped surface. The rear disc-shaped surface is adapted and arranged to be pushed by the user for delivering a set dose of the medicament 10.

The end cap 49 is preferably non-releasably secured to the drive sleeve 2. For example, the end cap 49 is snap-fitted to the drive sleeve 2. For this purpose, the drive sleeve 2 comprises a fixing element 50. The fixing element 50 is arranged close to the open proximal end 48 of the drive sleeve 2. The fixing element 50 comprises two oppositely arranged cutouts. The end cap 49 comprises a mating fixing element 51. The mating fixing element 51 comprises two oppositely arranged hooks. The hooks are resilient. In particular, the hooks are adapted and arranged to be radially deflectable. The fixing elements 50, 51 engage for non-releasably connecting the drive sleeve 2 and the end cap 49 to one another. More precisely, the end cap 49 and the drive sleeve 2 are engaged such that relative axial and rotational movement of the drive sleeve 2 and the end cap 49 is prevented.

In an alternative embodiment, the end cap 49 may be joined and/or glued to the drive sleeve 2, for example. Preferably, the end cap 49 is welded to the drive sleeve 2, e.g., by ultrasonic welding or heat welding. In a further alternative embodiment, end cap 49 and drive sleeve 2 may be formed unitarily. In these embodiments, the fixing elements 50, 51 may be redundant.

The medication delivery device 1 further comprises the previously mentioned dose setting sleeve 5.

The drive sleeve 2 is arranged at least partially within the dose setting sleeve 5. The dose setting sleeve 5 is rotatable with respect to the body 3 for setting a dose of the medication 10. The dose-setting sleeve 5 is not axially movable with respect to the body 3.

Figure 7:
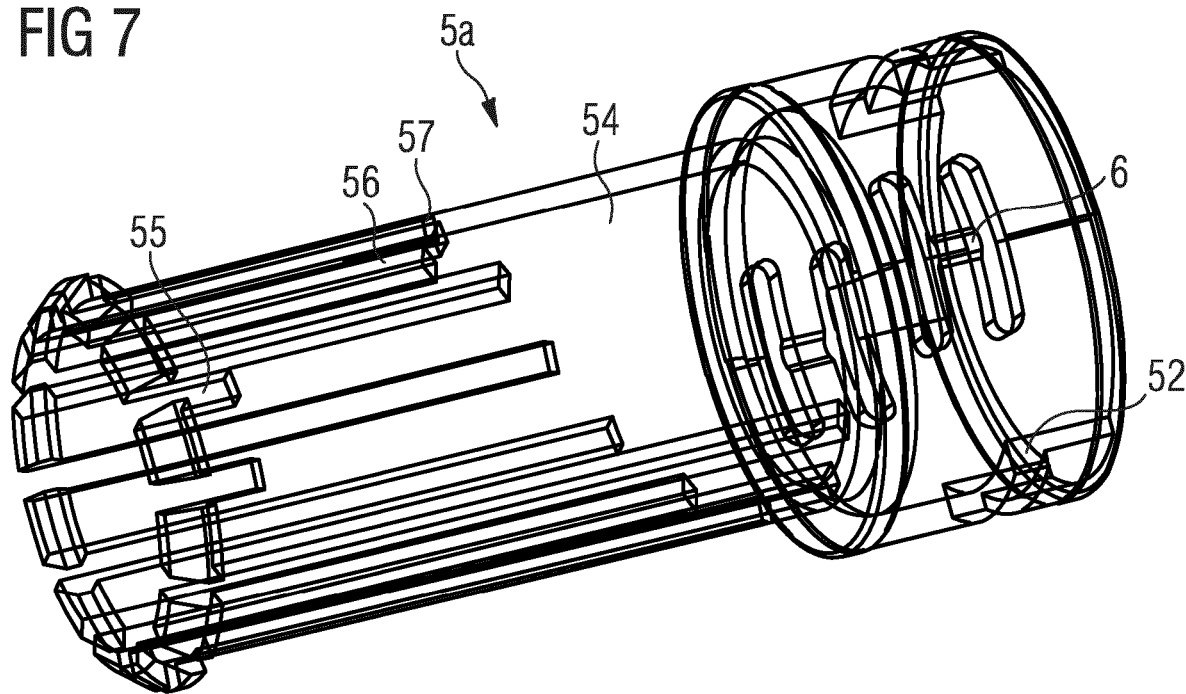
FIG. 7 schematically shows a perspective view of a dose setting sleeve front component of the medication delivery device.
Figure 8:
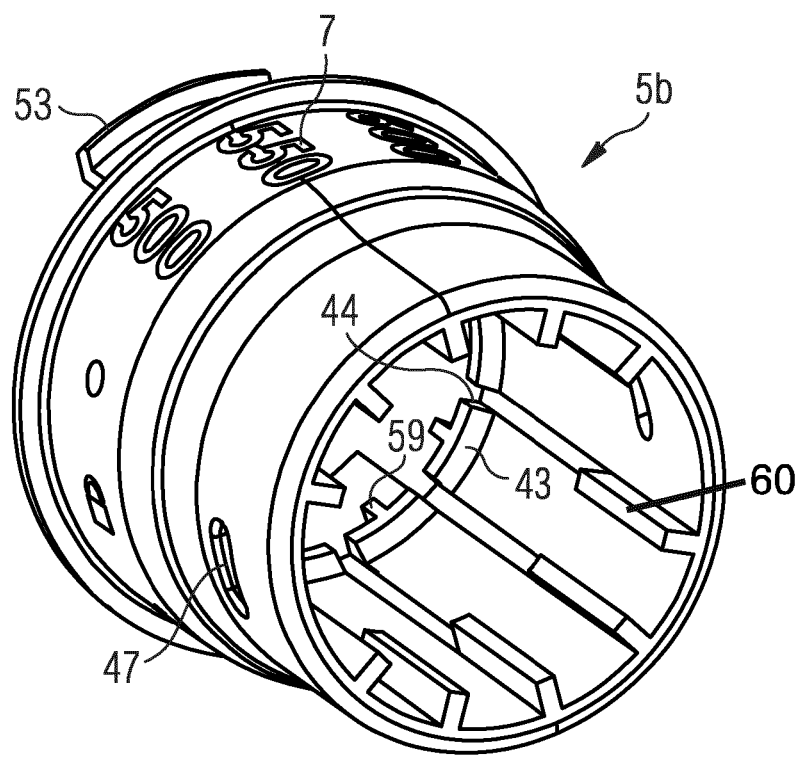
FIG. 8 schematically shows a perspective view of a dose setting sleeve rear component of the medication delivery device.

The dose setting sleeve 5 is tubular-shaped. In the embodiment shown in FIG. 3, the dose setting sleeve 5 consists of two components, a dose setting sleeve front component 5a and a dose setting sleeve rear component 5b. FIG. 7 shows a perspective view of the dose setting sleeve front component 5a. FIG. 8 shows a perspective view of the dose setting sleeve rear component 5b. The two components 5a, 5b are coupled, in particular non-releasably connected, to one another such that no relative movement between the two components 5a, 5b is possible. For example, the two components 5a, 5b can be snap-fitted to one another. In this way, relative axial and rotational movement of the two components 5a, 5b with respect to each other is prevented. In an alternative embodiment, the dose setting sleeve 5 can be a unitary component.

The dose setting sleeve front component 5a and the dose setting sleeve rear component 5b comprise mating engagement features 52, 53 which enable a snap-fit connection between the two components 5a, 5b. The mating engagement features 52, 53 comprise recesses arranged on the dose setting sleeve front component 5a and hook-shaped engagement features arranged on the dose setting sleeve rear component 5b. The hook-shaped engagement features are inserted into the mating recesses for non-releasably connecting the dose setting sleeve front component 5a and the dose setting sleeve rear component 5b. In an alternative embodiment, the mating engagement features 52, 53 may comprise hook-shaped engagement features arranged on the dose setting sleeve front component 5a and recesses arranged on the dose setting sleeve rear component 5b.

The dose setting sleeve 5 comprises a tubular body 54. The dose setting sleeve 5 comprises multiple tracks arranged on the tubular body 54. In the embodiment shown in FIGS. 3 and 7, the tracks are formed by slots in the tubular body 54. In an alternative embodiment, the tracks may be formed by grooves. Tracks being formed by grooves may provide an increased stability for the dose setting sleeve 5 over tracks being formed by slots.

The tracks have different lengths. The shortest track is the priming track 55. Further, the tracks comprise at least a first dosing track 56 having a first length which defines a first size of a dose. The tracks further comprise a second dosing track 57 having a second length defining a second dosing size. The second length is longer than the first length. Accordingly, the second dose size is larger than the first dose size. The tubular body 54 can comprise more than two dosing tracks. Each of the dosing tracks may correspond to a specific dose size. Accordingly, only discrete dose sizes can be set wherein the size of said discrete dose sizes depends on the length of the corresponding dosing track.

Each of the tracks 55, 56, 57 is linear. In other words, each of the tracks is parallel to the longitudinal axis.

The previously described engagement feature 37 of the drive sleeve 2 is configured to be received in the tracks 55, 56, 57 of the dose setting sleeve 5. When the engagement feature 37 is arranged in one of the tracks 55, 56, 57, a rotation of the drive sleeve 2 relative to the dose setting sleeve 5 is prevented.

In particular, the engagement feature 37 comprises two identical followers which are arranged parallel to each other. The tracks of the dose setting sleeve 5 are configured such that each of the followers can be received in a separate track. For example, the dose setting sleeve 5 comprises two identical priming tracks 55 configured to receive the followers. Further, each of the dosing tracks is arranged such that one of the followers can be received in said dosing track and that the respective other follower can be received in the adjacent dosing track. For example, to set the smallest possible dose, the engagement feature 37 has to be aligned with the first dosing track 56. Thereby, one of the followers is aligned with the first dosing track 56 and the other follower is aligned with the second dosing track 57. The distance by which the drive sleeve 2 can be moved proximally relative to the dose setting sleeve 5 is, in this configuration, limited by the length of the first dosing track 56. In general, when the two followers of the engagement feature 37 are aligned with two dosing tracks, the distance by which the drive sleeve 2 can be moved proximally relative to the dose setting sleeve 5 is limited by the length of the shorter one of the two dosing tracks.

The dose setting sleeve 5 further comprises the first stop face 43. The first stop face 43 is arranged at an inner surface of the dose setting sleeve 5. In particular, the first stop face 43 is arranged at an inner surface of the dose setting sleeve rear component 5b.

The first stop face 43 is an inwardly directed projection. The first stop face 43 faces in the proximal direction. The first stop face 43 is inclined relative to the longitudinal axis of the device 1. In particular, the first stop face 43 may be inclined by the same angle as the distal face 41 of the projection 40 arranged on the deflectable feature 39 of the drive sleeve 2. The first stop face 43 is shaped to enable the projection 40 of the deflectable feature 39 to slide over the first stop face 43. Thus, the deflectable feature 39 can override the first stop face 43. The drive sleeve 2 is configured to abut the first stop face 43 in the unprimed state of the device 1.

The dose setting sleeve 5 further comprises the second stop face 44. The second stop face 44 is formed by a distally facing face of the projection which also forms the first stop face 43. The second stop face 44 of the dose setting sleeve 5 is perpendicular to the longitudinal axis of the device 1. The second stop face 44 is configured to prevent a movement of the drive sleeve 2 in the proximal direction when the drive sleeve 2 abuts the second stop face 44 of the dose setting sleeve 5.

Accordingly, the dose setting sleeve 5 comprises a projection which defines two different axial stop. In contrast to the first stop face 43, the second stop face 44 of the dose setting sleeve 5 cannot be overridden without damaging a component of the assembly. In particular, a movement of the drive sleeve 2 in the proximal direction is prevented the second stop face 44 of the dose setting sleeve 5 when the projection 40 of the drive sleeve 2 abuts the second stop face 44. The drive sleeve 2 abuts the second stop face 44 after a dose has been fully delivered, as will be discussed later.

Further, the dose setting sleeve 5 comprises the previously mentioned deflectable detent 6. The deflectable detent 6 protrudes from the dose setting sleeve 5 in the radial outward direction. The deflectable detent 6 is deflectable in the radial direction.

The deflectable detent 6 is adapted and arranged to mechanically cooperate with the grooves 3d arranged on the inner surface of the body 3. The deflectable detent 6 is configured to releasably engage with the grooves 3d. It would be possible by means of an additional protrusion on the drive sleeve 2 to block the deflectable detent 6 from disengaging from the groove 3d in the unprimed condition so that it was not possible to rotate the dose setting sleeve 5 until priming was completed. This rotational block could be in addition to or perhaps in place of the side walls of the priming track 55 engaging the engagement feature 37. The deflectable detent 6 may have rounded edges to prevent jamming of the detent 6 with the grooves 3d.

The deflectable detent 6 has an azimuthal extension which must not exceed the azimuthal extension of the grooves 3d. In particular, the azimuthal extension of the deflectable detent 6 should be at least marginally smaller than the azimuthal extension of the grooves 3d.

During the first step of the dose setting operation, the dose setting sleeve 5 is rotated. Thereby, the deflectable detent 6 is subsequently disengaged from and engaged with the grooves 3d of the body 3. Each time the deflectable detent 6 is engaged with or disengaged from a groove 3d, an audible and/or tactile feedback is provided to a user.

The azimuthal position of the grooves 3d is in the body 3 and the azimuthal position dosing tracks 56, 57 in the dose setting sleeve 5 are adapted and arranged such that the deflectable detent 6 is engaged with a groove 3d when the engagement feature 37 of the drive sleeve 2 is aligned with a dosing track 56, 57. Thus, the engagement of the detent 6 with the grooves 3d in the body 3 help a user to align the engagement feature 37 with the dosing tracks 56, 57.

The grooves 3d in the body and the deflectable detent 6 may be shaped such that a rotation of the dose setting sleeve 5 relative to the body 3 is enabled only in one rotational direction. A counter-rotation of the dose setting sleeve 5 in the counter-rotational direction may not be possible as the deflectable detent 6 may not be enabled to override a side wall of the grooves 3d in the counter-rotational direction as this side wall may be steeper and/or less rounded that the side wall arranged in the rotational direction. Thereby, the user is prevented from re-engaging the engagement feature 37 with the priming track 55 by mistake.

The dose setting sleeve 5 further comprises multiple of the previously mentioned ribs 60 and a plurality of the further ribs 59. The ribs 60 are arranged at a proximal end of the dose setting sleeve 5 and extend in a longitudinal direction. Before priming, the slot 58 is engaged with one of the ribs 60, thereby preventing a rotation of the drive sleeve 2 relative to the dose setting sleeve 5.

Each of the further ribs 59 extends in the longitudinal direction. As discussed above, in the locked-out state, the slot 58 is engaged with one of the further ribs 59, thereby preventing a rotation of the dose setting sleeve 5 and the drive sleeve 2 relative to each other. The further ribs 59 are arranged distally of the second stop face 44 of the dose setting sleeve 5. After overriding the first stop face 43 of the dose setting sleeve 5, the drive sleeve 2 engages with the dose setting sleeve 5 by the slot 58 engaging with one of the further ribs 59, thereby locking the dose setting sleeve 5 and the drive sleeve 2 rotationally.

The dose setting sleeve 5 further comprises the window 47 which is configured for providing information about an operational state of the device 1. In particular, different sections of the drive sleeve 2 may be visible through the window 47 for indicating different states of the device 1. The window 47 is arranged in the dose setting sleeve rear component 5b.

Further, the dose setting sleeve 5 is configured for providing information about a set size of the dose of medication 10. For this purpose, symbols 7 are provided, e.g., printed or glued, on an outer surface of the dose setting sleeve 5. The symbols 7 are arranged circumferentially around the outer surface. In particular, a circumferentially arranged row of symbols 7 is provided on the outer surface of the dose setting sleeve 5. Of course, other arrangements of symbols 7 are possible.

The symbols 7 comprise numerals relating to the size of the set dose. In particular, the dose setting sleeve 5 and the body 3 are adapted and arranged such that the symbol 7 aligned with the marker 3e on the body 3 gives information concerning the size of the currently set dose.

In the following, operation of the medication delivery device 1 is described in detail in connection with FIGS. 9, 10, 11 and 12. Said figures show the body 3 in a cross-sectional view and the further components of the medication delivery device 1 in a perspective view.

FIG. 9 shows the device 1 as supplied from the manufacturer, i.e., in an unprimed state.

In the unprimed state a lock-symbol of the dose setting sleeve 5 may be aligned with the marker 3e of the body 3. Moreover, none of the colored rings 45, 46 is visible in the window 47 of the dose setting sleeve 5. Instead, the drive sleeve 2 and the dose setting sleeve 5 may be adapted and arranged such that the part of the drive sleeve 2 which comprises the two colored rings 45, 46 protrudes from the proximal end of the dose setting sleeve 5 such that both rings 45, 46 are fully visible. This may indicate to a user that the device 1 is in its unprimed state and that a priming operation needs to be carried out before a dose setting operation and/or a dose delivery operation can be performed.

In the unprimed state, there may be air in the body 3 or in the cartridge 11 containing the medication 10. In the unprimed state, there may be a gap between the piston rod 4 and the dose 17. The occurrence of air in the device 1 or of the gap may arise from manufacturing and/or assembly tolerances of the components of the device 1. The size of the gap may vary. However, in the delivery condition, i.e., when delivering a set dose of the medication 10, the gap between the piston rod 4 and the dose 17—or respectively air in the cartridge 11—may affect the dose accuracy. Especially for a device which is configured for delivering only one dose of medication, as is the case in the present device, a high dose accuracy is crucial.

For that reason, the device 1 may not be operated unless a priming operation was performed by the user. In particular, in the unprimed state, a dose setting operation is prevented as the engagement feature 37 of the drive sleeve 2 is arranged in the priming track 55 of the dose setting sleeve 5. Thereby, a rotation of the dose setting sleeve 5 relative to the drive sleeve 2 is prevented. As mentioned earlier, a rotational lock could alternatively also be accomplished by blocking, in the unprimed state, the deflectable detent 6 from an inward movement by an additional protrusion provided on the drive sleeve 5.

FIG. 10 shows the device 1 in its primed state, i.e., after a priming operation has been performed. For priming the device 1 and thus for bringing the device into its primed state, the user presses onto the end cap 49, thereby moving the piston rod 4 in the distal direction relative to the body 3. When the piston rod 4 is moved in the distal direction during the priming operation, air that may be present in the cartridge 11 in the unprimed state escapes from the device 1 through the needle 16. In its primed state, the device 1 is in a condition ready for setting and dispensing a dose of the medication 10. In its primed state, any tolerances from assembly and manufacturing have been removed. In particular, the gap between the piston rod 4 and the dose 17 has been removed in the primed state.

For priming the device 1, the user presses the end cap 49. As the end cap 49 is fixed to the drive sleeve 2, the drive sleeve 2 is moved in the distal direction relative to the body 3 during the priming operation. The drive sleeve 2 is engaged with the piston rod 4 via an engagement of the ratchet arms 38 with the ratchet teeth 34. The ratchet arm 38 and the ratchet teeth 34 are adapted and arranged such that a distal movement of the drive sleeve 2 is transferred into a distal movement of the piston rod 4. Accordingly, when the drive sleeve 2 travels into the distal direction during the priming operation, the piston rod 4 is also moved in the distal direction relative to the body 3. Thereby, the gap between the piston rod 4 and the dose 17 is closed.

The priming track 55 is adapted and arranged such that the distance by which the drive sleeve 2 travels in the distal direction during the priming operation is at least as long as the length of the priming track 55 and is at least as long of the combined longitudinal extension of the priming teeth 28a, 28b, respectively 28c, 28d. Thus, at the end of the priming operation, the engagement feature 37 is disengaged from the priming track 55. When the engagement feature 37 has been disengaged from the priming track 55, the drive sleeve 2 and the dose setting sleeve 5 are no longer rotationally locked to each other. Accordingly, it is now possible to rotate the dose setting sleeve 5 relative to the drive sleeve 2 and, therefore, to perform a dose setting operation.

The distance by which the drive sleeve 2 travels during the priming operation is chosen such that a different color coding is visible in the window 47 of the dose setting sleeve 5 at the end of the priming operation, thereby indicating that the device 1 is now in its primed state. For example, the first colored ring 45 may be visible in the window 47 in the primed state.

The distance by which the drive sleeve 2 travels during the priming operation is determined by the distance from the projection 40 arranged on the deflectable feature 39 of the drive sleeve 2 to the first stop face 43 of the dose setting sleeve 5. During the priming operation, the drive sleeve 2 is moved in the distal direction relative to the dose setting sleeve 5. Thus, during the priming operation, the projection 40 approaches the first stop face 43. When the projection 40 of the deflectable feature 39 of the drive sleeve 2 abuts the first stop face 43, the priming operation is finished. This abutment prevents a further movement of the drive sleeve 2, and thereby of the piston rod 4, in the distal direction. In order to move the drive sleeve 2, and thereby the piston rod 4, further in the distal direction, it would be necessary to override the first stop face 43 of the dose setting sleeve 5. In the primed state of the device 1, overriding the first stop face 43 is not possible as it is not possible for the deflectable feature 39 to be deflected inwardly due to the alignment of the section of maximum radial extension of the piston rod 4 with the projection 40. In other words, in the primed state, the piston rod 4 is arranged such that the piston rod 4 prevents the deflectable feature 39 from deflecting inwardly.

As the piston rod 4 is moved distally during priming, each of the claws 15, 15d of the non-returned ratchet 15 slides over two priming teeth 28a, 28b, 28c, 28d. Thereby, an audible and/or tactile feedback may be provided to a user. In the primed state, the claw 15b abuts the proximal face of the second priming tooth 28b.

In the primed state, as shown in FIG. 10, the piston rod 4 is arranged more distal than in the unprimed state of the device as shown in FIG. 9.

Now, the user can set the desired dose of the medication 10. For that purpose, the user can perform a dose setting operation. FIG. 11 shows the device 1 after a dose setting operation has been performed.

The dose setting operation comprises two steps which have to be initiated each by a user operated action. For a first step of the dose setting operation, the user grips the dose setting sleeve 5 and rotates it in a rotational direction, e.g., the anti-clockwise direction. A rotation of the dose setting sleeve 5 in the opposite direction may be prevented due to the specific shape of the sidewalls of the grooves 3d of the body 3. Alternatively, in a rotational direction, only the first groove 3d corresponding to a priming position and the last groove 3d corresponding to the maximum settable dose may be provided with a rotational lock, i.e., a user must start dialing from the smallest dose, but then is free to increase and/or decrease. However, it may not possible to dial from "prime" directly to "max" with just one click. Similarly, it might be preferable to prevent dialing from "max" back to "prime" position. This might help to prevent the user from dialing an accidental "overdose" of the maximum dose. The device may be designed such that it takes more effort to dial the largest dose, compared to the smallest. In an alternative design, a rotation in the opposite direction may be allowed, e.g., to reduce the set dose.

In the primed state, i.e., after the priming operation is completed and before the dose setting operation has been started, the deflectable detent 6 is engaged in one of the grooves 3d of the body 3. When the dose setting sleeve is rotated, the deflectable detent 6 is disengaged from said groove 3d and, afterwards, engages the groove 3d which is adjacent to said groove 3d in the rotational direction. During the rotation of the dose setting sleeve 5, the detent 6 engages with and disengages from the grooves 3d along the body 3. When the detent 6 disengages from a groove 3d, it is deflected radially inwardly. When the detent 6 engages the adjacent groove 3d, it relaxes in the radial outward direction. Each time the detent 6 is engaged with one of the grooves 3d, the engagement feature 37 is aligned with a track of the dose setting sleeve 5. The engagement of the deflectable detent 6 with one of the grooves 3d may provide an audible and/or tactile feedback to a user. This feedback may indicate that the device 1 is in a configuration wherein the second step of the dose setting operation can be initiated as the engagement feature 37 is aligned with one of the tracks, i.e., that one of the discrete doses has been set.

During the first step of the dose setting operation, the dose setting sleeve 5 is rotated relative to the drive sleeve 2 and relative to the piston rod 4. Neither the drive sleeve 2 nor the piston rod 4 are moved relative to the body 3 during the first step of the dose setting operation. The engagement feature 37 is misaligned from the priming track 55 when the dose setting sleeve 5 starts to rotate relative to the drive sleeve 2. For performing the second step of the dose setting operation, the user pulls the end cap 49 and thereby the drive sleeve 2 in the proximal direction relative to the body 3. Thereby, the engagement feature 37 is moved in the proximal direction relative to the dose setting sleeve 5. Such a movement of the engagement feature 37 is only possible if, at the end of the first step of the priming operation, the engagement feature 37 has been aligned with the start of one of the dosing tracks 56, 57 of the dose setting sleeve 5. In case the engagement feature 37 is not aligned with the start of one of the dosing tracks 56, 57, the engagement feature 37 would be blocked by the dose setting sleeve 5 from its movement in the proximal direction. Accordingly, in this case, the second step of the dose setting operation could not be initiated.

When, at the end of the first step, the engagement feature 37 is aligned with the start of one of the tracks 56, 57 of the dose setting sleeves 5, the engagement feature 37 travels along the corresponding dosing track 56, 57 when the drive sleeve 2 is pulled in the proximal direction. The engagement of the ratchet arm 38 of the drive sleeve 2 and the ratchet teeth 34 of the piston rod 4 is adapted and arranged such that the drive sleeve 2 is moved relative to the piston rod 4 in the proximal direction as the ratchet arm 38 is enabled to slide over the ratchet teeth 34. Accordingly, the piston rod 4 is not moved relative to the body 3 during the second step of the dose setting operation. An unwanted distal movement of the piston rod 4 relative to the body 3 is prevented by the abutment between the claws 15b, 15d of the non-return ratchet 15 with the second priming tooth 28b and respectively the fourth priming tooth 28d. As the drive sleeve 2 is now moved relative to the piston rod 4 in the axial direction, the third axial section 4c of the piston rod 4 having the maximum radial extension is no longer aligned with the projection 40 arranged on the deflectable feature 39. Thus, the piston rod 4 no longer prevents a deflection of the deflectable feature 39. Thus, it will later be possible to lock out the device 1 after the dose is dispensed by overriding the first stop face 43.

The length by which the drive sleeve 2 is moved in the proximal direction relative to the piston rod 4 during the second step of the dose setting operation is determined by the length of the dosing track 56, 57 to which the engagement feature 37 is engaged. This length corresponds to the size of the dose which will be delivered. At the end of the second step of the dose setting operation, the engagement feature 37 abuts a proximal end of the corresponding dosing track 56, 57, thereby preventing a further proximal movement of the drive sleeve 2.

Now, the device 1 is ready for delivering the set dose of the medication. FIG. 12 shows the device after the dose has been dispensed. For delivering the set dose, the user pushes onto the end cap 49. The drive sleeve 2, and thus the piston rod 4, are moved in the distal direction relative to the body 3 and relative to the dose setting sleeve 5. When the piston rod 4 is moved distally, the piston rod 4 pushes the dose 17 further into the cartridge 11, thereby expelling medication 10 from the needle 16.

Close to the end of the dose dispensing operation, the distal face 41 of the projection 40 of the deflectable feature 39 of the drive sleeve 2 abuts the first end stop 43 of the dose setting sleeve 5. As discussed above, the third axial section 4c of the piston rod 4 having the maximum radial extension has been moved relative to the deflectable feature 39 during the dose setting operation. Thus, the section 4c having the maximum radial extension no longer prevents a deflection of the deflectable feature 39. Accordingly, the deflectable feature 39 is now enabled to deflect inwardly and thus, the projection 40 of the drive sleeve 2 can override the first stop face 43 of the dose setting sleeve 5.

After overriding the first stop face 43, i.e., at the end of the dose delivery operation, the deflectable feature 39 returns elastically into its outward position. The projection 40 arranged on the deflectable feature 39 now abuts the second stop face 44 of the dose setting sleeve 5. This abutment is designed to prevent a further movement of the piston rod 4 in the proximal direction. Accordingly, it is not possible to set another dose of medication 10. Moreover, the slot 58 is now engaged with one of the further ribs 59, thereby preventing a rotation of the drive sleeve 2, and thus the piston rod 4, relative to the dose setting sleeve 5.

Moreover, at the end of the dose delivery operation, the end cap 49 which is engaged with the drive sleeve 2 may abut the proximal end of the dose setting sleeve 5. Thereby, a further movement of the drive sleeve 2, and thus of the piston rod 4, in the distal direction relative to the dose setting sleeve 5 is prevented. Accordingly, the drive sleeve 2 and the piston rod 4 can neither be moved proximally nor distally relative to the body 3 and relative to the dose setting sleeve 5.

The drive sleeve 2 and the piston rod 4 are further rotationally locked relative to the body 3 by the engagement of the claws 15b, 15d of the non-return ratchet 15 with the piston rod 4.

The device 1 is now locked. No further dose of the medication 10 can be set and dispensed from the device 1. The remaining amount of the medication 10 is discarded along with the device 1. The window 47 in the dose setting sleeve 5 displays the second colored ring 46 for indicating that the dose was correctly set and dispensed.

What is claimed is:

1. Assembly for a medication delivery device that is configured to perform a dose setting operation, comprising:
   a dose setting sleeve,
   a drive sleeve,
   a plunger,
   a body,
   a deflectable feature, and
   a first stop face,
   wherein the dose setting sleeve is adapted and arranged to be rotated with respect to the body for setting a dose of the medication,
   wherein the drive sleeve is configured such that the plunger is pushed in a distal direction relative to the body by the drive sleeve when the drive sleeve moves in the distal direction relative to the body,
   wherein the dose setting sleeve comprises a first dosing track having a first length and defining a first size of a dose and at least a second dosing track having a second length and defining a second size of a dose, wherein the first length is different from the second length and the first size is different from the second size,
   wherein the drive sleeve comprises an engagement feature configured to engage with one of the dosing tracks,
   wherein the assembly is configured such that the dose setting operation comprises a first step wherein the engagement feature is aligned with one of the dosing tracks and a second step wherein the engagement feature is moved along the aligned dosing track,
   wherein overriding of the first stop face by the deflectable feature is operative for producing a locked-out state in which movement of the drive sleeve relative to the body is prevented, and
   wherein in an initial state of the assembly before setting of a dose for the first time, the plunger is arranged such that the plunger directly prevents deflection of the deflectable feature, thereby preventing the deflectable feature from overriding the first stop face.

2. Assembly according to claim 1, wherein the dose setting sleeve is rotated relative to the drive sleeve during the first step of the dose setting operation.

3. Assembly according to claim 1, wherein the drive sleeve is movable in a purely linear manner relative to the dose setting sleeve during the second step of the dose setting operation.

4. Assembly according to claim 1, further comprising user-operated means for initiating each of the first step and the second step of the dose setting operation.

5. Assembly according to claim 1, wherein the assembly is configured such that the second step of the dose setting operation is prevented if the engagement feature is not aligned with one of the dosing tracks.

6. Assembly according to claim 1, wherein the assembly is configured to perform a dose dispensing operation for dispensing a dose of a medication from the medication delivery device,
   wherein the assembly is configured such that, during the first step of the dose setting operation, a size of the dose which is to be dispensed in the dose dispensing operation is selected by aligning the engagement feature with one of the dosing tracks, and
   wherein the assembly is configured such that, during the second step of the dose setting operation, the assembly is prepared to dispense a dose of the size selected in the first step by moving the drive sleeve relative to the dose setting sleeve by a distance corresponding to length of the dosing track to which the engagement feature has been aligned in the first step.

7. Assembly according to claim 1, wherein, during the second step of the dose setting operation, a rotation of the dose setting sleeve relative to the drive sleeve is prevented by the engagement of the engagement feature with one of the dosing tracks.

8. Assembly according to claim 1, wherein the plunger is adapted and arranged to be linearly moved in a distal direction with respect to the body for dispensing the medication, and wherein the drive sleeve is mechanically engaged with the plunger such that a linear movement of the drive sleeve relative to the plunger in a proximal direction is enabled and such that a linear movement of the drive sleeve relative to the plunger in a distal direction is prevented.

9. Assembly according to claim 1, wherein the assembly comprises a longitudinal axis, wherein the engagement feature is a protrusion extending from the drive sleeve in a radial direction away from the longitudinal axis, and wherein the dosing tracks on the dose setting sleeve are formed by grooves or slots in the dose setting sleeve.

10. Assembly according to claim 1, wherein the assembly comprises a longitudinal axis, and wherein the first dosing track and the second dosing track are parallel to the longitudinal axis.

11. Assembly according to claim 1, wherein the plunger comprises a section having a maximum radial extension,
   wherein in the initial state of the assembly before a dose is set for the first time, the section having the maximum radial extension is aligned with the deflectable feature, thereby preventing the deflection of the deflectable feature.

12. Assembly for a medication delivery device that is configured to perform a dose setting operation, comprising:
   a dose setting sleeve,
   a drive sleeve,
   a plunger, and
   a body,
   wherein the dose setting sleeve is adapted and arranged to be rotated with respect to the body for setting a dose of the medication,
   wherein the drive sleeve is configured such that the plunger is pushed in a distal direction relative to the body by the drive sleeve when the drive sleeve moves in the distal direction relative to the body,
   wherein the dose setting sleeve comprises a first dosing track having a first length and defining a first size of a dose and at least a second dosing track having a second length and defining a second size of a dose, wherein the first length is different from the second length and the first size is different from the second size,
   wherein the drive sleeve comprises an engagement feature configured to engage with one of the dosing tracks,
   wherein the assembly is configured such that the dose setting operation comprises a first step wherein the engagement feature is aligned with one of the dosing tracks and a second step wherein the engagement feature is moved along the aligned dosing track,
   wherein the assembly is configured to perform a priming operation wherein a priming dose is dispensed from the device, wherein the priming operation has to be performed before a dose setting operation can be performed for the first time, and
   wherein the dose setting sleeve comprises a priming track having a length which defines a size of a priming dose which has to be dispensed before the dose setting operation can be performed for the first time.

13. Assembly according to claim 12, wherein the priming operation is performable by a single manually-operated step.

14. Assembly according to claim 12, wherein the assembly is configured such that, during the priming operation, the drive sleeve is moved relative to the dose setting sleeve either purely linearly or helically in the distal direction.

15. Medication delivery device comprising an assembly having:
   a dose setting sleeve,
   a drive sleeve,
   a plunger,
   a body,
   a deflectable feature, and
   a first stop face,
   wherein the dose setting sleeve is adapted and arranged to be rotated with respect to the body for setting a dose of the medication,
   wherein the drive sleeve is configured such that the plunger is pushed in a distal direction relative to the body by the drive sleeve when the drive sleeve moves in the distal direction relative to the body,
   wherein the dose setting sleeve comprises a first dosing track having a first length and defining a first size of a dose and at least a second dosing track having a second length and defining a second size of a dose, wherein the first length is different from the second length and the first size is different from the second size,
   wherein the drive sleeve comprises an engagement feature configured to engage with one of the dosing tracks, and
   wherein the assembly is configured such the dose setting operation comprises a first step wherein the engagement feature is aligned with one of the dosing tracks and a second step wherein the engagement feature is moved along the aligned dosing track,
   wherein the medication delivery device is a variable-dose, single-use device,
   wherein overriding of the first stop face by the deflectable feature is operative for producing a locked-out state in which movement of the drive sleeve relative to the body is prevented, and wherein in an initial state of the assembly before setting of a dose for the first time, the plunger is arranged such that the plunger directly prevents deflection of the deflectable feature, thereby preventing the deflectable feature from overriding the first stop face.

\* \* \* \* \*